US009597612B2

(12) United States Patent
Yabuhara et al.

(10) Patent No.: US 9,597,612 B2
(45) Date of Patent: Mar. 21, 2017

(54) ANALYSIS DEVICE INCLUDING SOLID-PHASE EXTRACTION MATERIAL FILLING AND DISCHARGING MECHANISMS

(71) Applicant: Hitachi High-Technologies Corporation, Tokyo (JP)

(72) Inventors: Tadao Yabuhara, Tokyo (JP); Izumi Waki, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 154 days.

(21) Appl. No.: 14/416,787

(22) PCT Filed: Jul. 25, 2013

(86) PCT No.: PCT/JP2013/070232
§ 371 (c)(1),
(2) Date: Jan. 23, 2015

(87) PCT Pub. No.: WO2014/017607
PCT Pub. Date: Jan. 30, 2014

(65) Prior Publication Data
US 2015/0182877 A1    Jul. 2, 2015

(30) Foreign Application Priority Data

Jul. 25, 2012  (JP) ................................. 2012-164467

(51) Int. Cl.
*B01D 15/38* (2006.01)
*G01N 1/40* (2006.01)
(Continued)

(52) U.S. Cl.
CPC ....... *B01D 15/3804* (2013.01); *B01D 15/206* (2013.01); *B01D 15/424* (2013.01);
(Continued)

(58) Field of Classification Search
CPC .... G01N 1/405; G01N 30/08; G01N 30/6091; G01N 35/025; G01N 35/02; B01D 15/206; B01D 15/3804; B01D 15/424
See application file for complete search history.

(56) References Cited

U.S. PATENT DOCUMENTS 5,585,068 A * 12/1996 Panetz ................. G01N 35/025
                                                                422/547
6,177,008 B1 * 1/2001 Treiber .................. B01D 15/08
                                                                210/198.2
(Continued)

FOREIGN PATENT DOCUMENTS

EP        1159597       8/2007
JP       56147067      11/1981
(Continued)

OTHER PUBLICATIONS

Extended European Search Report received in corresponding European Application No. 13822990.1 dated Feb. 17, 2016.
(Continued)

*Primary Examiner* — Natalie Huls
(74) *Attorney, Agent, or Firm* — Mattingly & Malur, PC

(57) ABSTRACT

Provided is an analyzer performing solid-phase extraction of a measurement component (i.e., component to be measured) in a sample solution while decreasing an amount of waste generated and reducing a running cost. The analyzer includes: a solid-phase extraction container having a body part to receive a sample solution containing a measurement component of analytical target and a discharge passage to discharge the sample solution. Herein, the discharge passage is to be filled with a solid-phase extraction material for subjecting the measurement component to solid-phase extraction. The analyzer further includes a supplying mechanism for a solid-phase extraction material; a filter supplying mechanism; a determining mechanism for filling position; a
(Continued)

discharging mechanism for discharging the filter and the solid-phase extraction material after the solid-phase extraction of the measurement component; and a container cleaning mechanism for cleaning the solid-phase extraction container from which the solid-phase extraction material is removed.

15 Claims, 13 Drawing Sheets

(51) Int. Cl.
G01N 35/02 (2006.01)
B01L 3/02 (2006.01)
G01N 30/08 (2006.01)
B01D 15/20 (2006.01)
B01D 15/42 (2006.01)
G01N 30/60 (2006.01)

(52) U.S. Cl.
CPC ............ B01L 3/0275 (2013.01); G01N 1/405 (2013.01); G01N 30/08 (2013.01); G01N 35/025 (2013.01); B01L 2200/025 (2013.01); B01L 2200/0631 (2013.01); B01L 2200/0668 (2013.01); B01L 2300/0681 (2013.01); G01N 30/6091 (2013.01)

(56) References Cited

U.S. PATENT DOCUMENTS

| | | | | |
|---|---|---|---|---|
| 6,541,273 | B1* | 4/2003 | Plaisance | B01D 15/265 210/198.2 |
| 6,723,236 | B2* | 4/2004 | Fisk | B01D 15/424 210/198.2 |
| 6,770,246 | B1* | 8/2004 | Husek | B01L 3/0275 210/263 |
| 9,176,037 | B2* | 11/2015 | Kanda | G01N 1/405 |
| 9,207,152 | B2* | 12/2015 | Nogami | G01N 1/4055 |
| 9,372,135 | B1* | 6/2016 | Benner | G01N 1/405 |
| 2002/0182114 | A1* | 12/2002 | Ingenhoven | B01L 3/0275 422/534 |
| 2004/0229346 | A1 | 11/2004 | Kohara et al. | |
| 2005/0191760 | A1 | 9/2005 | Heath et al. | |
| 2008/0064115 | A1* | 3/2008 | Hiramatsu | B01D 15/00 436/178 |
| 2009/0221080 | A1 | 9/2009 | Tajima | |
| 2012/0121464 | A1* | 5/2012 | Nogami | G01N 1/405 422/68.1 |
| 2012/0206713 | A1* | 8/2012 | Nogami | G01N 35/025 356/39 |
| 2013/0040403 | A1* | 2/2013 | Tikanoja | G01N 1/405 436/501 |
| 2013/0130401 | A1* | 5/2013 | Kanda | G01N 1/405 436/178 |
| 2013/0323138 | A1* | 12/2013 | Demmitt | B01J 19/0046 422/242 |
| 2014/0137671 | A1* | 5/2014 | Yabuhara | G01N 1/405 73/863.01 |

FOREIGN PATENT DOCUMENTS

| | | |
|---|---|---|
| JP | 2004333401 | 11/2004 |
| JP | 2006007081 | 1/2006 |
| JP | 2007017155 | 1/2007 |
| JP | 2011089924 | 5/2011 |
| JP | 2012002593 | 1/2012 |
| WO | 2007029616 | 3/2007 |

OTHER PUBLICATIONS

International Search Report in PCT/JP2013/070232, dated Oct. 15, 2013.

* cited by examiner

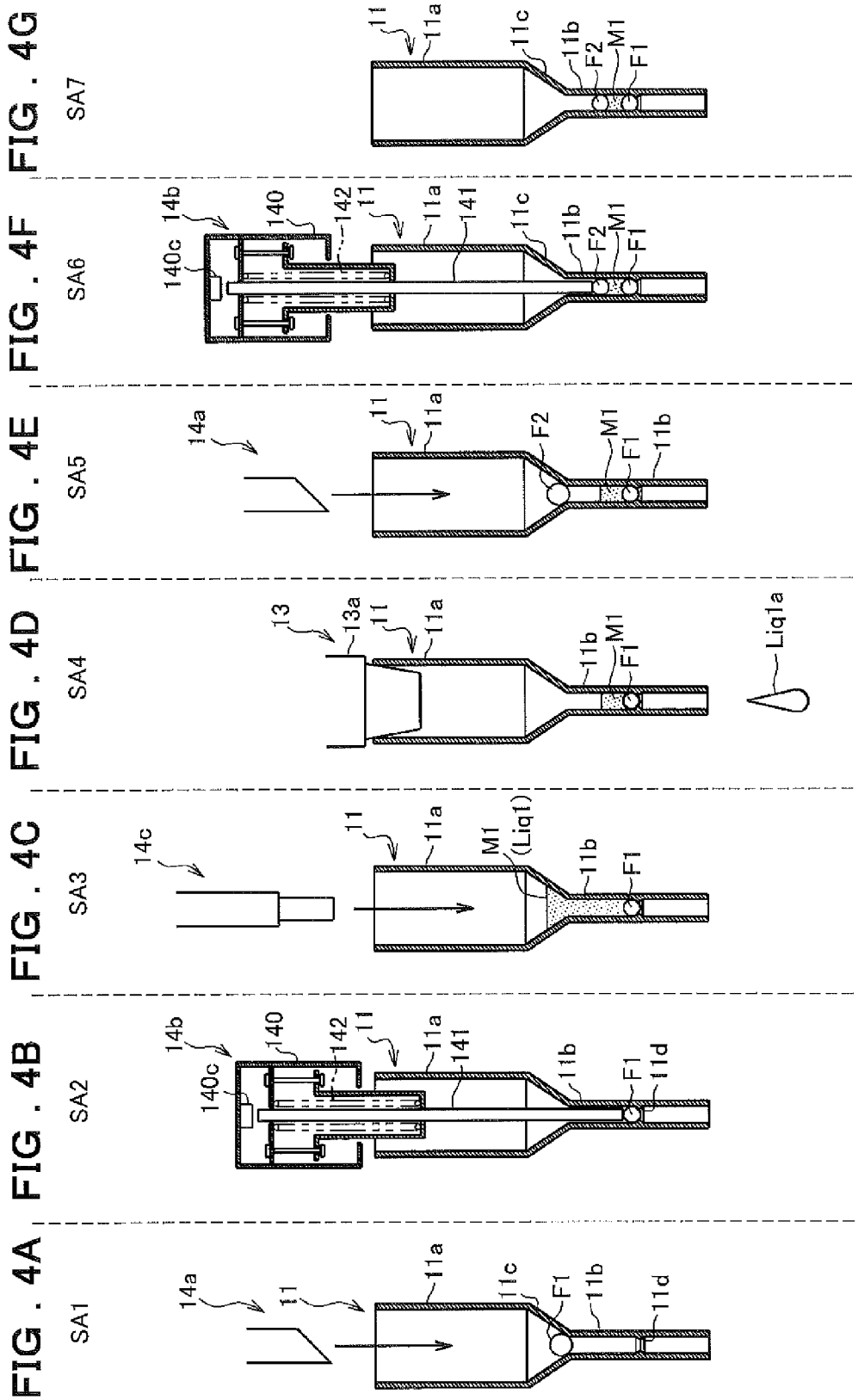

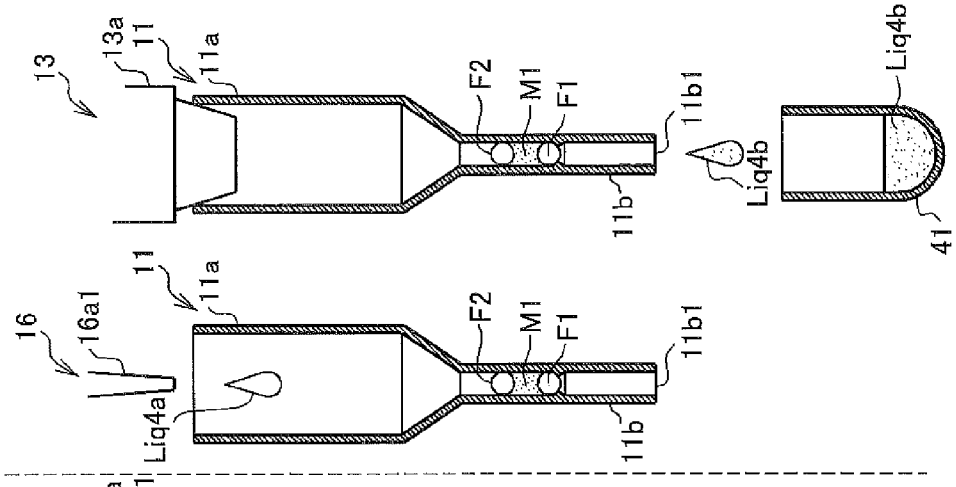
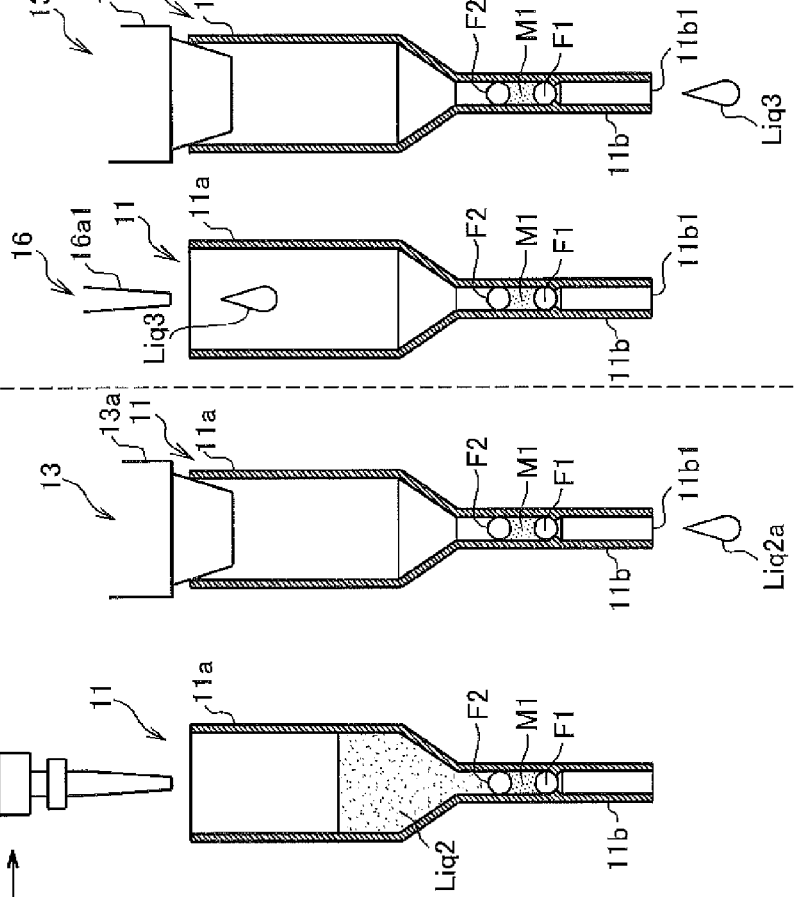
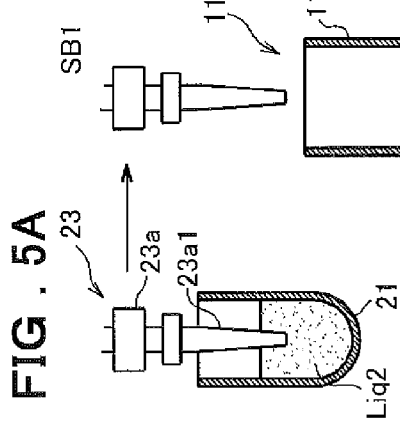

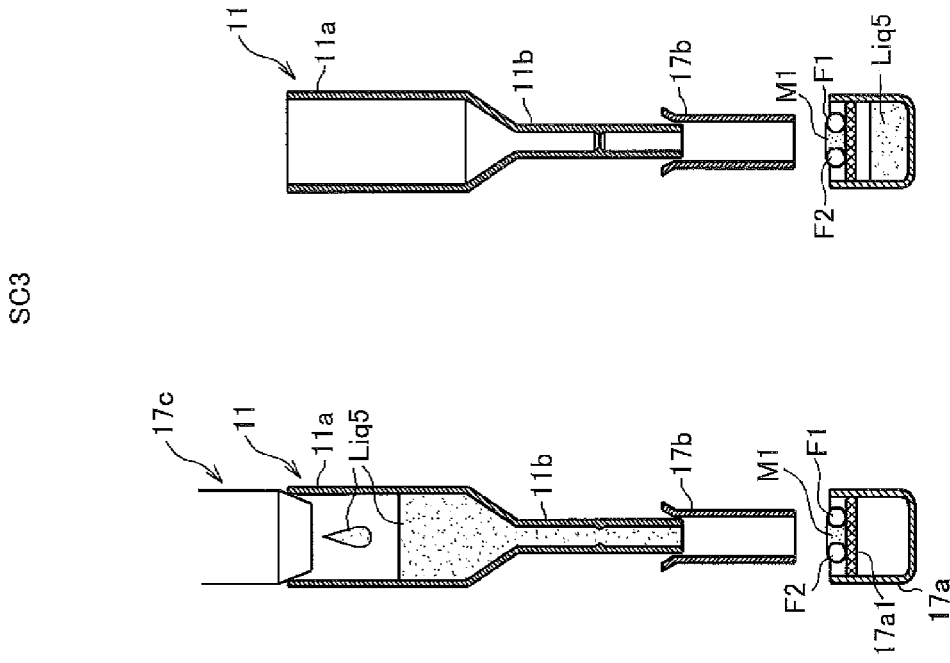
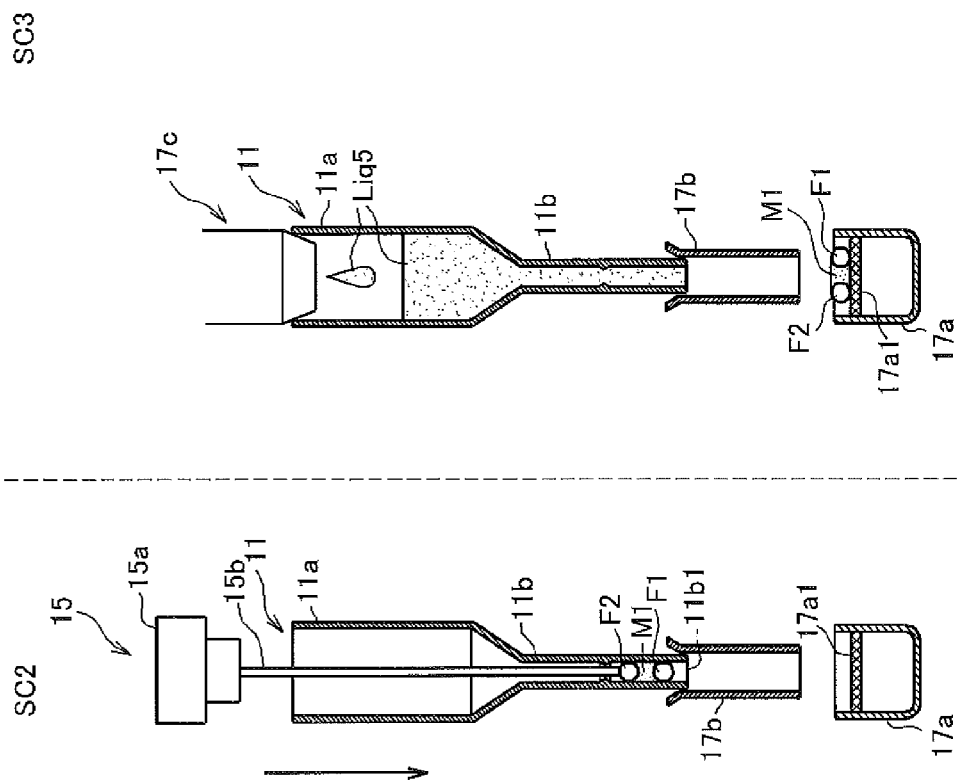
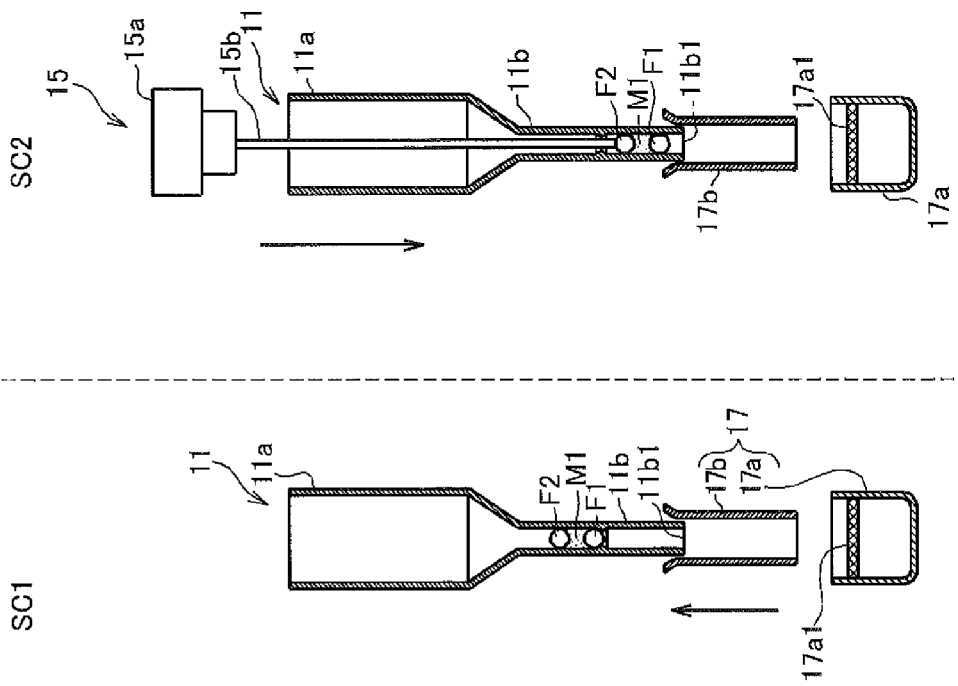

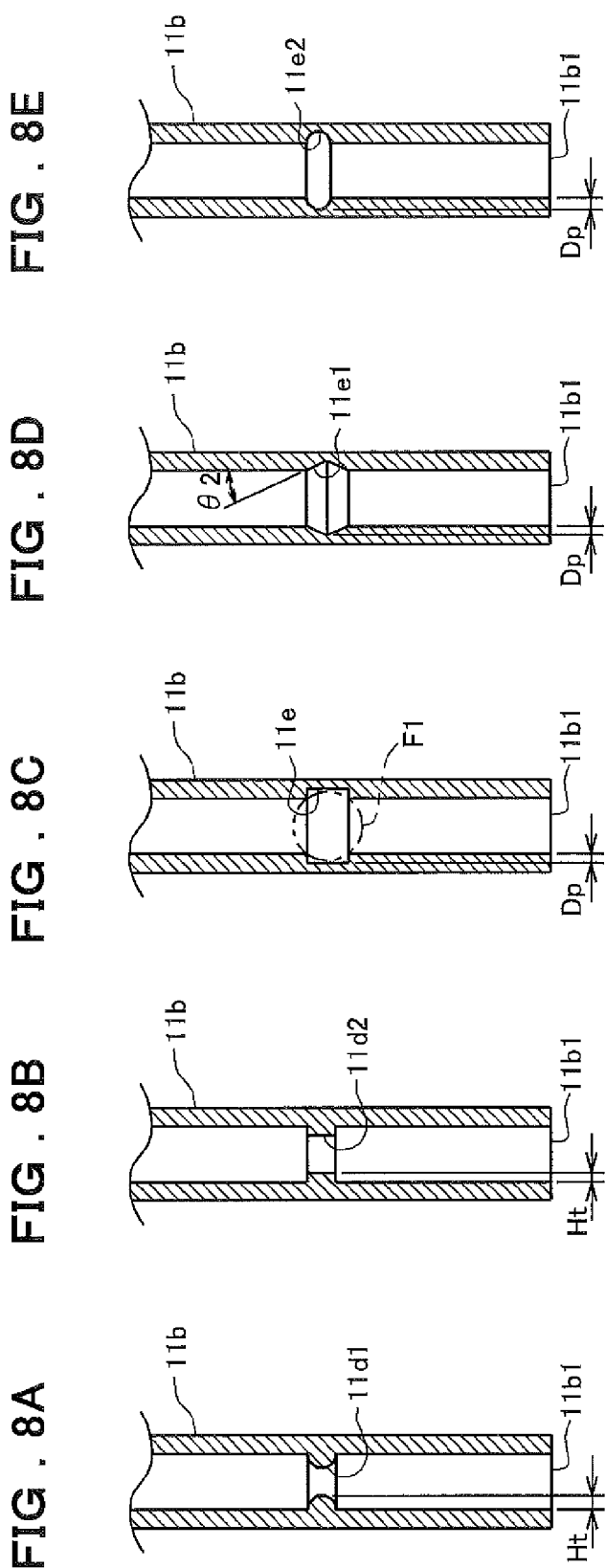

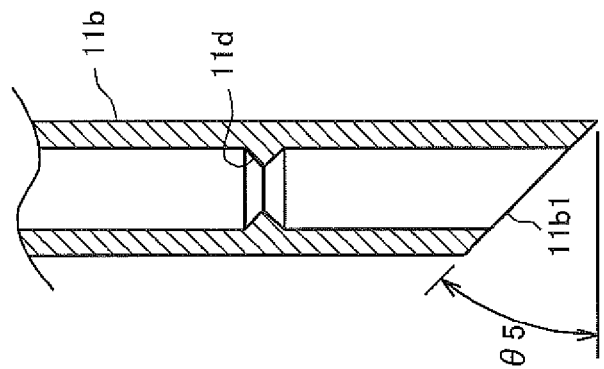
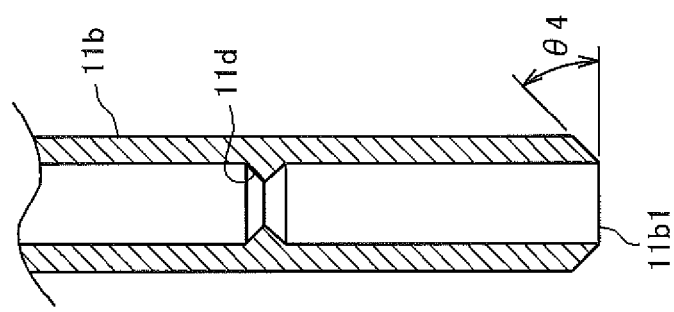
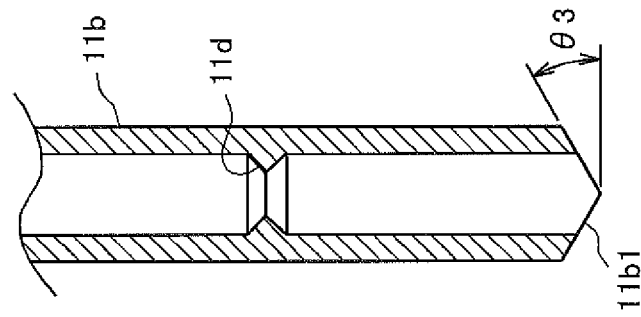

ANALYSIS DEVICE INCLUDING SOLID-PHASE EXTRACTION MATERIAL FILLING AND DISCHARGING MECHANISMS

TECHNICAL FIELD

The present invention relates to an analysis device (hereinafter, referred to as an analyzer).

BACKGROUND ART

Solid-phase extraction is a general process in which a solid phase (i.e., solid-phase extraction material) is used to separate a measurement component (i.e., a component to be measured) from impurities in a sample solution, depending on physical and chemical characteristics thereof. The solid-phase extraction is used in various analytical techniques (e.g., liquid chromatography, mass spectrometry) in order to purify a measurement component by removing impurities that prevent analysis.

Examples of a sample (or sample solution) that can be used for the analysis include urine, blood, and water. When the sample solution passes through a solid-phase extraction material, an affinity between a measurement component in the sample solution and the surface of the solid-phase extraction material may be high. In this case, the measurement component in the sample solution is selectively adsorbed. Accordingly, the measurement component can be purified or enriched.

A typical solid-phase extraction process includes three steps: an adsorption step of causing a measurement component in a sample solution to be adsorbed on a solid-phase extraction material; a cleaning step of removing impurities other than the measurement component adsorbed on the solid-phase extraction material; and an elution step of eluting the adsorbed measurement component from the solid-phase extraction material.

In the adsorption step, the measurement component is adsorbed on the solid-phase extraction material, and components preventing the analysis (i.e., impurities) flow out without being adsorbed. However, some impurities may be adsorbed on the solid-phase extraction material. Consequently, the adsorbed impurities should be removed in the cleaning step.

In the elution step, an eluent is used to separate the purified measurement component from the solid-phase extraction material. In addition, the post-separation eluate containing the measurement component is sent to an analyzer, where a signal intensity of the measurement component is measured.

As described above, the solid-phase extraction is carried out in the order of the adsorption step, the cleaning step, and the elution step. Accordingly, the impurities are removed and the measurement component is purified.

Further, as a solid-phase extraction kit, widely used are, for example, a syringe-type solid-phase extraction cartridge in which a solid-phase extraction material is interposed between filters in a syringe, and a 96-well solid-phase extraction cartridge in which a solid-phase extraction material is interposed between filters in a container for a 96-well microplate.

Examples of a device that automatically performs the above adsorption, cleaning, and elution steps include: a device disclosed in Patent Literature 1 that uses a pressurizing mechanism to apply pressure on a sample solution, thereby making the sample solution flow through a solid-phase extraction material; a solid-phase extraction device disclosed in Patent Literature 2 that uses a pressure-reducing mechanism to make a sample solution flow through a solid-phase extraction material; and a solid-phase extraction device disclosed in Patent Literature 3.

Further, Patent Literature 4 discloses solid-phase extraction cartridges used for the analyzers disclosed in, for example, Patent Literatures 1 and 2.

CITATION LIST

Patent Literatures

Patent Literature 1: JP2011-089924A
Patent Literature 2: JP2006-7081A
Patent Literature 3: EP Patent Application Publication No. 1159597
Patent Literature 4: U.S. Pat. No. 6,723,236

SUMMARY OF INVENTION

Technical Problem

Patent Literature 1 recites "the used solid-phase extraction cartridge 101 can be disposed of at position n" (see paragraph [0028]). In this way, a used solid-phase extraction material is conventionally wasted together with the solid-phase extraction cartridge. Generally speaking, the size of a container for solid-phase extraction (i.e., a solid-phase extraction container) is several dozen times larger than the size of a solid-phase extraction material. As a result, the disposal volume of the solid-phase extraction cartridge increases and a user burden due to the disposal becomes large. Further, users have to keep various commercially available syringe-type solid-phase extraction cartridges and dispose of the cartridges. This results in the increase in consumable costs for the solid-phase extraction cartridges, a solid-phase extraction container, filling a solid-phase extraction material, the solid-phase extraction material, and filters.

Moreover, once a cartridge is replaced as a unit, a solid-phase extraction material and a filter should also be replaced. Unfortunately, this increases costs of replacing the solid-phase extraction material and the filter, resulting in the increase in a running cost for an analyzer.

In addition, the solid-phase extraction device disclosed in Patent Literature 2 uses the 96-well solid-phase extraction cartridge disclosed in Patent Literature 4. In the same manner as in the case of the analyzer disclosed in Patent Literature 1, the disposal volume of the 96-well solid-phase extraction cartridge after solid-phase extraction increases. Accordingly, a burden on users becomes larger.

Further, in the case of the analyzer disclosed in Patent Literature 2, the 96-well solid-phase extraction cartridge is also used once and thrown away. For users, this results in the increase in consumable costs for the 96-well solid-phase extraction cartridges, a solid-phase extraction container, filling a solid-phase extraction material, the solid-phase extraction material, and filters.

In addition, Patent Literature 3 discloses a solid-phase extraction device performing on-line solid-phase extraction. The solid-phase extraction device disclosed in Patent Literature 3 can use a solid-phase extraction cartridge several times. When carryover is taken into consideration, the solid-phase extraction cartridge should be frequently replaced. Further, even in the case of the solid-phase extraction device disclosed in Patent Literature 3, a solid-phase extraction container, a solid-phase extraction material, and a filter as one set are also used once and thrown away after usage of the solid-phase extraction cartridge in the same manner as in the case of the devices disclosed in Patent Literatures 1 and 2. That is, the analyzer disclosed in Patent Literature 3 also increases costs for a solid-phase extraction container, filling a solid-phase extraction material, the solid-phase extraction material, and filters. Hence, a running cost becomes higher. Moreover, a disposal volume of the solid-phase extraction cartridge increases, thereby making a burden on users large.

In addition, Patent Literature 4 discloses the structure of a solid-phase extraction cartridge. This solid-phase extraction cartridge, however, has a taper on the inner wall surface at the release hole side. Accordingly, it is difficult to recycle the solid-phase extraction cartridge alone by disposing of a solid-phase extraction material and a filter from the inside to the outside of the solid-phase extraction cartridge. That is, the solid-phase extraction cartridge disclosed in Patent Literature 4 is supposed to be disposed of after its usage. Even if the solid-phase extraction cartridge disclosed in Patent Literature 4 is used for the devices discloses in, for example, Patent Literatures 1 to 3, a disposal volume of the solid-phase extraction cartridge still increases. Thus, a burden on users is not decreased. Further, this case also increases costs for a solid-phase extraction container, filling a solid-phase extraction material, the solid-phase extraction material, and filters. Hence, a running cost is not decreased.

In short, there has been no analyzer that can decrease a consumable cost for a solid-phase extraction cartridge and a disposal volume of the solid-phase extraction cartridge, the consumable cost and disposal volume increasing a burden on users.

It is an object of the present invention to provide an analyzer that has a function of subjecting a measurement component in a sample solution to solid-phase extraction while capable of decreasing an amount of waste generated and reducing a running cost to be low.

Solution to Problem

The present inventors have conducted research on recycling of a solid-phase extraction container in an analyzer so as to make it possible to reduce a consumable cost and a disposal volume caused by disposal of a solid-phase extraction cartridge, the consumable cost and disposal volume increasing a burden on users. The present inventors have found the following mechanisms that can be integrated in the analyzer so as to realize the above mentioned object. Examples of the mechanisms include: a filling mechanism for automatically filling the cartridge with a solid-phase extraction material; a discharging mechanism for automatically discharging the post-solid-phase-extraction material from a release hole of the solid-phase extraction container; and a container cleaning mechanism for automatically cleaning the solid-phase extraction container from which the solid-phase extraction material is removed. The present inventors have also found a preferable shape of the solid-phase extraction container that can be used for the above filling, discharging, and container cleaning mechanisms. Accordingly the above findings have realized the present invention.

Specifically, an analyzer according to an aspect of the present invention includes: a solid-phase extraction container including: a body part to receive a sample solution containing a measurement component of analysis target; and a discharge passage to discharge the sample solution introduced from the body part. Herein, the discharging passage is filled with a solid-phase extraction material used for subjecting the measurement component to solid-phase extraction. The analyzer further includes a supplying mechanism for solid-phase extraction material, the mechanism being used to supply the solid-phase extraction material to the solid-phase extraction container; a filter supplying mechanism for supplying a filter to the solid-phase extraction container; a determining mechanism for filling position, the mechanism being used to determine filling positions of the filter and the solid-phase extraction material; a discharging mechanism for discharging the filter and the solid-phase extraction material from a release hole of the solid-phase extraction container after the measurement component in the sample solution is subjected to the solid-phase extraction; and a container cleaning mechanism for cleaning the solid-phase extraction container from which the solid-phase extraction material is removed.

Advantageous Effects of Invention

The present invention provides an analyzer that has a function of subjecting a measurement component in a sample solution to solid-phase extraction while capable of decreasing an amount of waste generated and reducing a running cost to be low.

BRIEF DESCRIPTION OF DRAWINGS

FIGS. 4A to 4G illustrate a step of filling a solid-phase extraction material. FIG. 4A shows the first step. FIG. 4B shows the second step. FIG. 4C shows the third step. FIG. 4D shows the fourth step. FIG. 4E shows the fifth step. FIG. 4F shows the sixth step. FIG. 4G shows the seventh step.

FIGS. 5A to 5C illustrate a solid-phase extraction step. FIG. 5A depicts an adsorption step. FIG. 5B depicts a cleaning step. FIG. 5C depicts an elution step.

FIGS. 6A to 6C illustrate a container cleaning step. FIG. 6A shows a preparatory step. FIG. 6B shows a pushing step. FIG. 6C shows a cleaning step.

FIG. 8A is a cross-sectional view illustrating that a cross section shape has a semicircular convex portion. FIG. 8B is a cross-sectional view illustrating that a cross section shape has a rectangular convex portion. FIG. 8C is a cross-sectional view illustrating that a cross section shape has a concave portion. FIG. 8D is a cross-sectional view illustrating that a cross section shape has a triangular concave portion. FIG. 8E is a cross-sectional view illustrating that a cross section shape has a semicircular concave portion.

FIG. 9A is a cross-sectional view illustrating a shape where the periphery of a release hole is tilted toward both opposing ends. FIG. 9B is a cross-sectional view illustrating a shape where the periphery of a release hole is chamfered. FIG. 9C is a cross-sectional view illustrating a shape where the periphery of a release hole is tilted from one end to the other opposing end.

FIG. 11A shows the first step. FIG. 11B shows the second step. FIG. 11C shows the third step. FIG. 11D shows the fourth step. FIG. 11E shows the fifth step. FIG. 11F shows the sixth step. FIG. 11G shows the seventh step.

FIG. 13A shows the first step. FIG. 13B depicts the second step. FIG. 13C shows the third step.

EMBODIMENTS FOR CARRYING OUT PRESENT INVENTION

Hereinafter, embodiments of the present invention will be described in detail with reference to the attached drawings.

Embodiment 1

Figure 1:
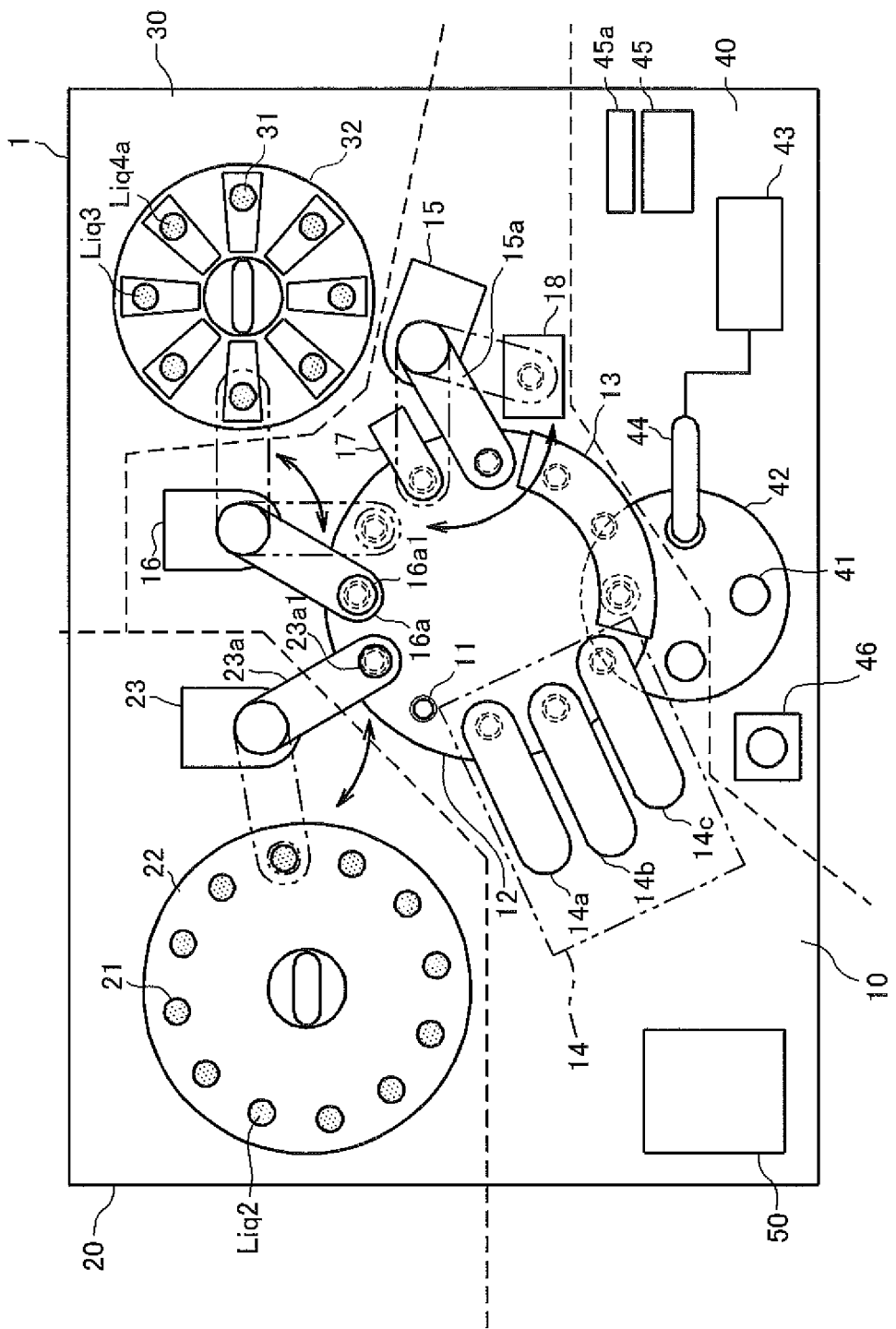
FIG. 1 illustrates how to configure an analyzer according to Embodiment 1.
Figure 2B:
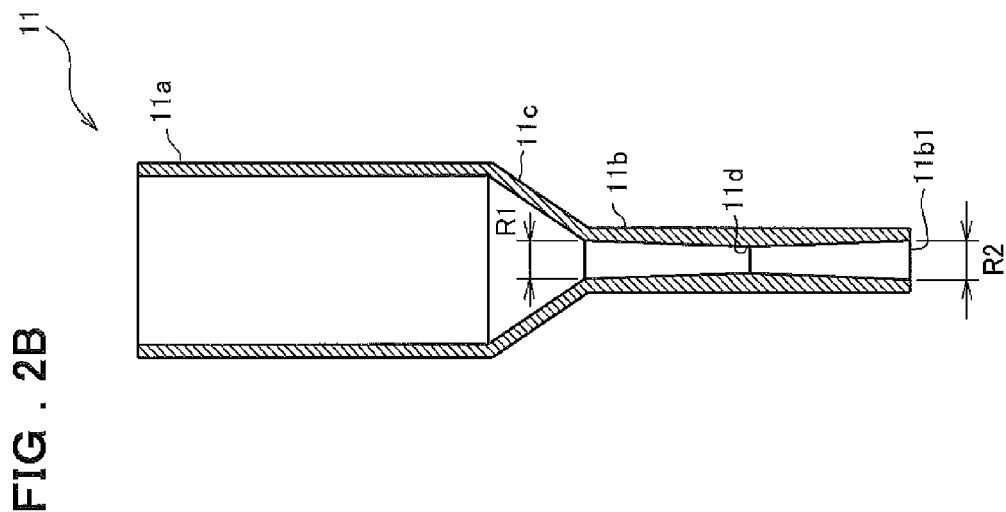
FIG. 2B is a cross-sectional view of a solid-phase extraction container in which the diameter of the internal surface of a discharge passage is decreased from the body part side and is increased toward the release hole side.
Figure 2A:
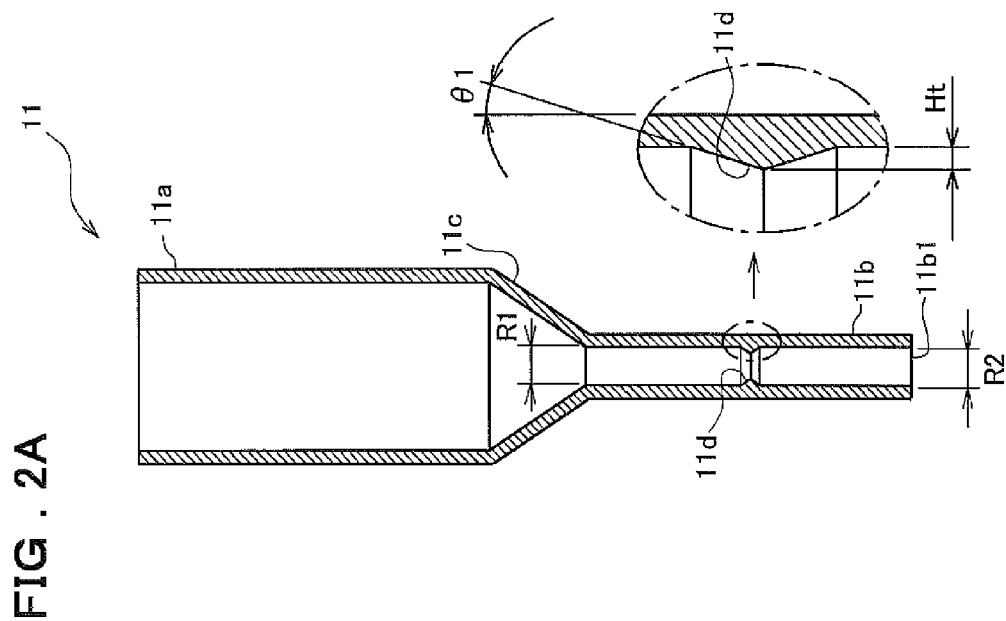
FIG. 2A is a cross-sectional view of a solid-phase extraction container having a convex portion.
Figure 3:
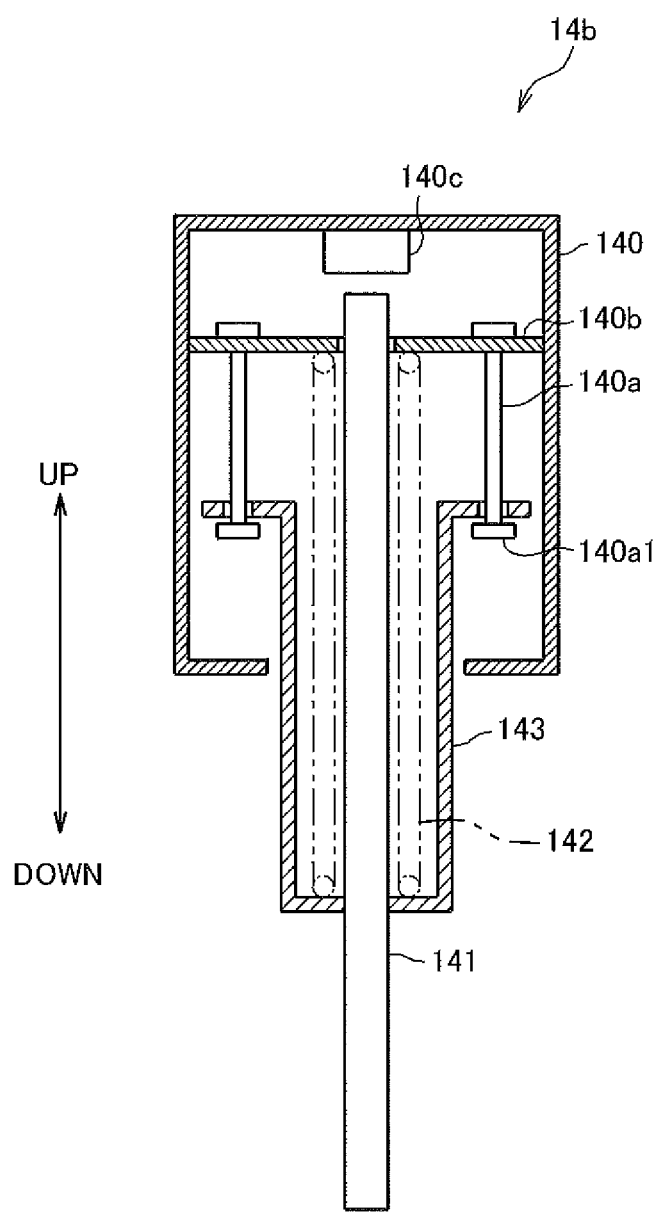
FIG. 3 is a cross-sectional view illustrating the structure of a determining mechanism for filling position.

FIG. 1 illustrates how to configure an analyzer according to Embodiment 1. In addition, FIG. 2A is a cross-sectional view of a solid-phase extraction container having a convex portion. FIG. 2B is a cross-sectional view of a solid-phase extraction container in which the internal diameter inside a discharge passage is decreased from the body part side to a middle, and is increased toward the release hole side. Further, FIG. 3 is a cross-sectional view illustrating the structure of a determining mechanism for filling position.

As shown in FIG. 1, the analyzer 1 according to Embodiment 1 includes: a processing section 10 for solid-phase extraction, a sample setting section 20, a reagent supplying section 30, and a sample analyzing section 40. The analyzer 1 is controlled by a control unit 50.

The sample setting section 20 includes: a sample transfer table 22 that turns sample containers 21 containing a solution (or sample solution Liq2) in which a measurement component of analysis target has been dissolved; and a sample dispensing mechanism 23 that moves the sample solution Liq2 to the processing section 10 from each sample container 21 transferred at a predetermined position by the sample transfer table 22.

Also, at a predetermined position in the vicinity of the sample transfer table 22 is installed, for example, an injection mechanism (not shown) that injects the sample solution Liq2 into each sample container 21. This injection mechanism is used to dispense the sample solution Liq2 into each sample container 21.

In addition, at a predetermined position in the vicinity of the sample transfer table 22, is installed a sample dispensing mechanism 23. The sample dispensing mechanism 23 is equipped with a sample dispensing arm 23a that can move a sample between the sample setting section 20 and the processing section 10 for solid-phase extraction. The sample dispensing arm 23a is disposed over the sample transfer table 22. An end portion of the arm has a suction mechanism 23a1 that sucks the sample solution Liq2. Here, in the sample dispensing mechanism 23, the suction mechanism 23a1 is used to suck the sample solution Liq2 contained in the sample container 21 transferred at a predetermined position by the sample transfer table 22. The sample dispensing arm 23a can be used to move the sucked sample solution Liq2 to the processing section 10 for solid-phase extraction.

The processing section 10 for solid-phase extraction includes: an extraction container table 12 having a plurality of containers (i.e., solid-phase extraction containers 11) mounted thereon, the table 12 turningly transferring the solid-phase extraction containers 11; an extraction processor 13; a filling mechanism 14 for solid-phase extraction material, the mechanism being capable of filling each solid-phase extraction container 11 with a solid-phase extraction material; a discharging mechanism 15 for discharging the solid-phase extraction material from the solid-phase extraction container 11; a reagent injection mechanism 16; and a container cleaning mechanism 17.

The extraction container table 12 is, for example, a circular disk. Its center portion may be rotatable and mounted on the analyzer 1. This construction allows the table 12 to turningly transfer the solid-phase extraction containers 11.

In addition, the solid-phase extraction container 11 according to Embodiment 1 is a cylindrical container (e.g., syringe) that can be filled with a solid-phase extraction material adsorbing a measurement component in the sample solution Liq2.

Note that in the processing section 10 according to Embodiment 1, the disk-shaped extraction container table 12 is configured to turningly transfer the solid-phase extraction containers 11. However, the present invention is not limited to this configuration. For example, the solid-phase extraction containers 11 may be arranged like a grid with predetermined spacing and may be transferred using a transfer arm (not shown). For example, the analyzer 1 may have a structure with 96 solid-phase extraction containers 11 in an arrangement of 12 rows×8 columns.

As shown in FIG. 2A, the solid-phase extraction container 11 includes: a substantially cylindrical hollow body part 11a having an open end; and a discharge passage 11b having an open release hole 11b1 at its tip portion, the passage being formed by reducing the diameter of the other end of the body part 11a. This diameter-reducing part 11c is used to continuously connect the body part 11a and the discharge passage 11b.

The sample solution Liq2 (see FIG. 1) is injected through the open end of the body part 11a. Then, the sample solution Liq2 that has been injected into the body part 11a passes through the discharge passage 11b to be discharged from the release hole 11b1.

Note that when the filter described hereinafter is packed, elastic force of the filter should be considered. In this regard, it is preferable to set an internal diameter R1 of the discharge passage 11b at the body part 11a side and an internal diameter R2 of the discharge passage 11b at the release hole 11b1 side, so as to satisfy the following relationship: "0.6× R1 (mm)≤R2≤1.4×R1 (mm)".

In addition, a portion of the internal surface of the discharge passage 11b has a convex portion 11d that is convex all around the circumference. The convex portion 11d has, for example, a triangular cross section shape. The convex portion 11d partially decreases the internal diameter of the discharge passage 11b.

Next, the solid-phase extraction material is supplied to the discharge passage 11b from the body part 11a side of the solid-phase extraction container 11. Then, the solid-phase extraction material is locked at the convex portion 11d.

The shape of the convex portion 11d is not limited. For example, a pressure applied to the filter described hereinafter is estimated based on a pressure applied when a measurement component is subjected to solid-phase extraction. In this case, the height Ht from the internal surface of the discharge passage 11b to the top of the triangular portion may be within a range of "0.1 (mm)≤Ht≤0.2×R1 (mm)". The inner surface angle θ1 when viewed from the top may be within a range of "0.1 (degree)≤θ1≤90 (degrees)". If the parameters are in the range as defined above, experiments demonstrate that the convex portion 11d suitably lock the solid-phase extraction material. Hence, it is preferable that the convex portion 11d has a protrusion with a height of 0.1 mm or more and "0.2×R1 (mm)" or less from the internal surface of the discharge passage 11b and has an internal surface angle of 0.1 degree or more and 90 degrees or less when viewed from the top.

Alternatively, as shown in FIG. 2B, a solid-phase extraction container 11 may have a structure in which an internal diameter inside the discharge passage 11b is gradually reduced from a first end at the body part 11a side and the internal diameter is gradually increased toward the release hole 11b1 from a top portion formed at an optional position. In this structure, the top portion is the convex portion 11d. Further, it is preferable to set an internal diameter R1 of the discharge passage 11b at the first end of the body part 11a side and an internal diameter R2 of the discharge passage 11b at a second end of the release hole 11b1 side, so as to satisfy a relationship: "0.6×R1 (mm)≤R2≤1.4×R1 (mm)" in the same manner as in the case of the solid-phase extraction container 11 illustrated in FIG. 2A.

Now, return to the description of FIG. 1. The analyzer 1 according to Embodiment 1 includes the filling mechanism 14 for solid-phase extraction material, the mechanism being capable of filling the solid-phase extraction container 11 with an unused solid-phase extraction material. The filling mechanism 14 includes: a filter supplying mechanism 14a for supplying to the solid-phase extraction container 11 a filter used to remove unwanted substances from a sample solution containing a measurement component; a supplying mechanism 14c for solid-phase extraction material, the mechanism being used to supply to the solid-phase extraction container 11 a solid-phase extraction material adsorbing the measurement component; and a determining mechanism 14b for filling position, the mechanism being used to determine filling positions of the filter and the solid-phase extraction material in the solid-phase extraction container 11.

The filter supplying mechanism 14a is disposed over the extraction container table 12 mounted on the analyzer 1. The filter supplying mechanism 14a causes, for example, a spherical filter to fall into the solid-phase extraction container 11. The supplying mechanism 14c for solid-phase extraction material is disposed over the extraction container table 12 mounted on the analyzer 1. Then, slurry prepared by dispersing powder of a solid-phase extraction material in a solution, is added dropwise to the solid-phase extraction container 11.

The determining mechanism 14b for filling position is disposed over the extraction container table 12 mounted on the analyzer 1. As shown in FIG. 3, the determining mechanism 14b includes a main body 140 that can move downward (i.e., toward the solid-phase extraction container 11 side) by means of an actuator (not shown). Also, this main body 140 includes a pin rod 141. The rod 141 can move downward from the main body 140 and is elastically supported by an elastic member (or spring 142) inside the main body 140. This spring 142 is configured to energize the rod 141 downward, and the rod 141 moves upward when predetermined upward force is applied to a tip of the rod 141.

The specific structure of the determining mechanism 14b is not limited. For example, the inside structure of the main body 140 includes: a vertical guide-rail 140a; and a movable cylinder 143 that vertically slides using the guide-rail 140a as a guide and has a closed lower end. The rod 141 is fixed while penetrating through the closed lower end of the movable cylinder 143. Then, the rod 141 and the movable cylinder 143 move as a unit. Note that the movable cylinder 143 has an upper opening.

In addition, the rod 141 penetrates through a hollow space of the movable cylinder 143. The rod 141 is surrounded by a spring 142 that is a compression spring. Further, the main body 140 includes a plate stopper 140b that locks the spring 142 at an upper side of the movable cylinder 143.

According to this configuration, the spring 142 is interposed under suitably compressed conditions between the closed end of the movable cylinder 143 and the plate stopper 140b of the main body 140. The spring 142 energizes the movable cylinder 143 and the rod 141 downward.

Note that a terminal 140a1, for example, may be formed to restrict downward movement of the movable cylinder 143 along the guide-rail 140a. In this case, it is possible to prevent the movable cylinder 143 from being derailed from the guide-rail 140a.

In addition, the rod 141 penetrates through the plate stopper 140b. Also, a pressure detection unit (or pressure sensor 140c) is mounted on an upper portion of the main body 140, the portion being on the axis of the rod 141.

The pressure sensor 140c is, for example, a sensor for detecting a pressure when one terminal of the rod 141 is in contact with the sensor. The pressure sensor 140c inputs detection signals to the control unit 50 (see FIG. 1) of the analyzer 1. The control unit 50 receives the input detection signals sent from the pressure sensor 140c and can thereby detect a pressure generated by the rod 141 while the rod 141 is in contact with the pressure sensor 140c.

In Embodiment 1, the solid-phase extraction container 11 has a structure illustrated in FIG. 2A or 2B; and the determining mechanism 14b of the filling mechanism 14 is constructed as indicated in FIG. 3.

Now, return to the description of FIG. 1. The extraction container table 12 mounted on the analyzer 1 is disposed below the sample dispensing arm 23a of the sample dispensing mechanism 23 and transfers the solid-phase extraction container 11 directly under the sample dispensing arm 23a. Then, the sample solution Liq2, which has been sucked from the sample container 21 in the sample setting section 20 by the suction mechanism 23a1 of the sample dispensing arm 23a, is discharged into the solid-phase extraction container 11.

Further, the extraction processor 13, the discharging mechanism 15, the reagent injection mechanism 16, and the container cleaning mechanism 17 are appropriately arranged at predetermined positions surrounding the extraction container table 12.

The extraction processor 13 has a pressure nozzle 13a (see FIG. 4D) that feeds high-pressure air and has a function of discharging the high-pressure air into the solid-phase extraction container 11 to pressurize the solid-phase extraction container 11.

The discharging mechanism 15 has a function of discharging the used solid-phase extraction material from the solid-phase extraction container 11. Note that the reference sign 15a denotes a work arm of the discharging mechanism 15.

The reagent injection mechanism 16 has a function of injecting into the solid-phase extraction container 11 a reagent (e.g., a cleaning reagent Liq3 that cleans the solid-phase extraction container 11; an eluent Liq4*a* that is used for solid-phase extraction of a measurement component) that is supplied from the reagent supplying section 30.

In addition, the container cleaning mechanism 17 cleans the solid-phase extraction container 11 used for the solid-phase extraction.

The details of the extraction processor 13, discharging mechanism 15, reagent injection mechanism 16, and container cleaning mechanism 17 will be described hereinafter.

The sample analyzing section 40 includes: an eluate transfer table 42 that rotationally transfers a container (or eluate storing container 41) receiving an eluate containing a measurement component extracted from the solid-phase extraction container 11; a liquid transfer unit 44 that sends to an analyzing unit 43 the eluate contained in the eluate storing container 41; a computation system 45 that calculates analysis results based on data (or measured values) as obtained using the analyzing unit 43 by measuring the measurement component in the eluate; an external communication interface 45*a* that outputs the analysis results calculated by the computation system 45 to an output unit (e.g., a monitor, a printer) (not shown); and a container storage unit 46 that stores the eluate storing containers 41.

Preferably, the eluate storing container 41 receives a measurement component-containing eluate that falls dropwise from the solid-phase extraction container 11 on the extraction container table 12 fixed to the analyzer 1. In view of this, the eluate transfer table 42 is preferably disposed below the extraction container table 12.

The analyzing unit 43 is a device that obtains data by analyzing a measurement component in the eluate, the measurement component having been extracted in the processing section 10 for solid-phase extraction. Herein, the analyzing unit 43 is configured to fit the usage of the analyzer 1.

Examples of a method for analyzing a measurement component in the analyzing unit 43 include, but are not limited to, liquid chromatography and mass spectrometry.

Then, the measured values obtained by the analyzing unit 43 are input into the computation system 45. The computation system 45 calculates the results of the measurement component analysis based on the input measured values. In addition, depending on the need, the computation system 45 uses the external communication interface 45*a* to output the calculated analysis results to a monitor and/or a printer (not shown). Meanwhile, the control unit 50 and/or the computation system 45, if necessary, make the analysis results stored in a storage medium (e.g., a hard disk drive (HDD)) (not shown).

Note that unused eluate storing containers 41 are stored in the container storage unit 46 and, as needed, are set on the eluate transfer table 42 by using a transfer apparatus (e.g., a transfer arm) (not shown).

The reagent supplying section 30 includes a reagent transfer table 32 that rotationally transfers reagent containers 31 filled with a cleaning reagent Liq3 which is used to clean the solid-phase extraction container 11, or the eluent Liq4*a* which is used for solid-phase extraction of a measurement component in a sample solution. The reagent transfer table 32 is disposed below a reagent injection arm 16*a* of the reagent injection mechanism 16 and transfers each reagent container 31 to a position directly under the reagent injection arm 16*a*. The reagent injection arm 16*a* has a suction mechanism 16*a*1 that sucks the cleaning reagent Liq3 and/or the eluent Liq4*a* from the reagent container 31. The cleaning reagent Liq3 or the eluent Liq4*a* that has been sucked from the corresponding reagent container 31 is then discharged into the solid-phase extraction container 11 on the extraction container table 12 fixed to the analyzer 1. Because of this, the reagent injection arm 16*a* is positioned over the extraction container table 12.

In addition, the reagent supplying section 30 includes a refill mechanism (not shown) that refills an empty reagent container 31, from which the cleaning reagent Liq3 or the eluent Liq4*a* has been sucked, with a fresh cleaning reagent Liq3 or eluent Liq4*a*.

Note that examples of a method for refilling the cleaning reagent Liq3 or eluent Liq4*a* include, but are not limited to, a method for replacing a whole reagent container 31 and a method for supplying only a solution (e.g., the cleaning reagent Liq3, the eluent Liq4*a*) to the reagent container 31.

By using the above configuration, the reagent supplying section 30 can continually supply the cleaning reagent Liq3 and/or the eluent Liq4*a*.

Further, in an preferable configuration, an input device such as a personal computer (not shown) connected to the external communication interface 45*a*, for example, is used to send to and write in the computation system 45 information on the reagent (e.g., the cleaning reagent Liq3, the eluent Liq4*a*) in the reagent container 31 set on the reagent transfer table 32 and information on a position of the reagent container 31 on the reagent transfer table 32. The control unit 50 obtains from the computation system 45 the information on the refillable reagents and the information on the position of the reagent container 31. By doing so, the control unit 50 can identify which reagent is added to the reagent container 31 and where the reagent container 31 is positioned on the reagent transfer table 32.

Alternatively, a bar code that indicates the refilled reagent information may be attached to the reagent container 31 and the reagent injection arm 16*a* may be equipped with a bar-code reader. Then, the reagent injection arm 16*a* may read the bar code on the reagent container 31, and this information may be sent to the control unit 50. In this configuration, the control unit 50 can identify the reagent in the reagent container 31 on the basis of the information read from the bar code by the reagent injection arm 16*a*.

Further, the reagent container 31 may have a chip such as an information rewritable RFID (Radio Frequency IDentification) chip, and the reagent injection arm 16*a* may have a reader that reads information written in the chip. Then, the reagent injection arm 16*a* may read the chip information and this information may be sent to the control unit 50. Furthermore, a refill mechanism (not shown) may write in this chip the information that identifies which reagent (e.g., the cleaning reagent Liq3, the eluent Liq4*a*) is added to the reagent container 31. In this configuration, the reagent injection arm 16*a* reads the information written in the chip and sends the information to the control unit 50. This enables the control unit 50 to identify the reagent in the reagent container 31.

Overall, FIG. 1 illustrates that the analyzer 1 according to Embodiment 1 includes: the processing section 10 for solid-phase extraction, the sample setting section 20, the reagent supplying section 30, and the sample analyzing section 40. The analyzer 1 is controlled by the control unit 50. Then, the control unit 50 makes it possible to analyze a measurement component while appropriately executing the steps including: a step of filling a solid-phase extraction container 11 with a solid-phase extraction material (i.e., a filling step for solid-phase extraction material); a step of subjecting the measurement component contained in a sample solution to solid-phase extraction in the solid-phase extraction container 11 filled with the solid-phase extraction material (i.e., a solid-phase extraction step); and a step of cleaning the solid-phase extraction container 11 after the solid-phase extraction (i.e., a container cleaning step).

FIG. 4 illustrates a step of filling a solid-phase extraction container with a solid-phase extraction material while the control unit controls a filling mechanism for a solid-phase extraction material. FIG. 4A shows the first step. FIG. 4B shows the second step. FIG. 4C shows the third step. FIG. 4D shows the fourth step. FIG. 4E shows the fifth step. FIG. 4F shows the sixth step. FIG. 4G shows the seventh step.

As shown in FIGS. 4A to 4G, the step of filing a solid-phase extraction material includes 7 steps (i.e., the first to seventh steps), and the solid-phase extraction container 11 is filled with a solid-phase extraction material M1. Note that FIGS. 4A to 4G illustrate the step of filing a solid-phase extraction material. In this step, a solid-phase extraction container 11 is filled with solid-phase extraction material M1 powder. Hereinafter, with reference to FIGS. 4A to 4G, the step of filing a solid-phase extraction material will be described in detail (see FIGS. 1 to 3, if necessary).

In the first step SA1 shown in FIG. 4A, the control unit 50 controls the extraction container table 12 to transfer the solid-phase extraction container 11 directly under the filter supplying mechanism 14a. Next, the control unit 50 controls the filter supplying mechanism 14a to supply a filter (or bottom filter F1) to the solid-phase extraction container 11. The filter according to Embodiment 1 is spherical and flexible. The filter supplying mechanism 14a has a function of causing the spherical filter (or bottom filter F1) to fall down in the solid-phase extraction container 11 that has been transferred directly under the filter supplying mechanism 14a.

Then, the filter supplying mechanism 14a puts the spherical bottom filter F1 into the body part 11a of the solid-phase extraction container 11. The filter has a diameter larger than the internal diameter inside the discharge passage 11b. The bottom filter F1 thus stops at an interface between the diameter-reducing part 11c and the discharge passage 11b.

Note that the shape of the filter (or bottom filter F1) is not limited to a spherical shape. Examples of the shape include a cylinder, a cylinder with a taper, and a cylinder with a step. In addition, examples of a cross section shape of the filter include polygonal shapes such as trapezoidal, rhombic, square, and rectangular shapes.

In the second step SA2 shown in FIG. 4B, the control unit 50 controls the extraction container table 12 to transfer the solid-phase extraction container 11 containing the bottom filter F1 directly under the determining mechanism 14b for filling position.

Next, the control unit 50 moves the main body 140 of the determining mechanism 14b downward. The rod 141 is then inserted into the solid-phase extraction container 11 containing the bottom filter F1. The rod 141 further enters the discharge passage 11b while pushing forward the bottom filter F1 into the discharge passage 11b.

When the bottom filter F1 encounters the convex portion 11d, the filter movement is prevented. At that time, upward resistance force is generated at a terminal of the rod 141. This resistance force involves subjecting the rod 141-supporting spring 142 to elastic compression, thereby stopping the forward movement of the rod 141.

In this way, the spring 142 is subjected to elastic compression to regulate the bottom filter F1-pushing force of the rod 141, which prevents excessive pressure from being imposed on the bottom filter F1. Consequently, the above configuration suppresses plastic deformation of the bottom filter F1.

In other words, it is preferable that the spring 142 is configured to apply elastic force to the rod 141 at a degree not to subject the bottom filter F1 to plastic deformation.

Specifically, the spring 142 preferably has smaller elastic force than the bottom filter F1.

Further, the spring 142 applies downward elastic force to the rod 141. Next, the rod 141 together with the main body 140 move downward to make the filter or bottom filter F1) move along the internal surface of the discharge passage 11b. That is, the spring 142 applies elastic force to the rod 141 in a traveling direction of the rod 141. Then, the rod 141 uses the elastic force applied by the spring 142 to make the bottom filter F1 move along the internal surface of the discharge passage 11b.

According to this configuration, the bottom filter F1 does not cause plastic deformation, and the rod 141 can make the bottom filter F1 move along the internal surface of the discharge passage 11b.

The main body 140 may move downward while the rod 141 stops its forward movement. In this case, the rod 141 moves upward relative to the main body 140, and the other terminal of the rod 141 is in contact with the pressure sensor 140c. The pressure sensor 140c sends to the control unit 50 a detection signal generated when this terminal of the rod 141 pressurizes the sensor. That is, the pressure sensor 140c is a pressure detection unit that detects, as a pressure, the force applied to the rod 141 by the bottom filter F1 locked at the convex portion 11d of the discharge passage 11b.

The control unit 50 receives the input detection signals sent from the pressure sensor 140c and can thereby detect a pressure generated by the rod 141 while the rod 141 is in contact with the pressure sensor 140c. When this pressure reaches a predetermined value, the main body 140 is made to move upward so as to dislocate the main body 140 from the solid-phase extraction container 11.

The bottom filter F1 still stays at the discharge passage 11b of the solid-phase extraction container 11, so that the position of the bottom filter F1 is determined.

In this way, in the second step SA2, the filter (or bottom filter F1) is supplied from the filter supplying mechanism 14a to the solid-phase extraction container 11; and the determining mechanism 14b for filling position sets the position of the bottom filter F1 at the convex portion 11d of the discharge passage 11b. Accordingly, the bottom filter F1 is set in the solid-phase extraction container 11. Hence, the filter filling mechanism according to Embodiment 1 includes the filter supplying mechanism 14a and the determining mechanism 14b for filling position.

In the third step SA3 shown in FIG. 4C, the control unit 50 controls the extraction container table 12 to transfer the solid-phase extraction container 11 containing the bottom filter F1 directly under the supplying mechanism 14c for solid-phase extraction material.

Next, the control unit 50 controls the supplying mechanism 14c to fill the solid-phase extraction container 11 with a solid-phase extraction material M1. Specifically, the supplying mechanism 14c pours, into the body part 11a of the solid-phase extraction container 11, a slurry of extraction material liquid Liq1 in which the solid-phase extraction material M1 powder is dispersed.

The extraction material liquid Liq1, which has been poured into the body part 11a of the solid-phase extraction container 11, flows into the discharge passage 11b. Then, the extraction material liquid Liq1 is stopped by the bottom filter F1 and accumulates on the bottom filter F1.

In the fourth step SA4 shown in FIG. 4D, the control unit 50 controls the extraction container table 12 to transfer the solid-phase extraction container 11 containing the extraction material liquid Liq1 directly under the extraction processor 13. Next, the control unit 50 controls the extraction processor 13 to fit the pressure nozzle 13a of the extraction processor 13 into the body part 11a of the solid-phase extraction container 11. Then, the control unit 50 controls the extraction processor 13 to feed high-pressure air into the solid-phase extraction container 11 from the tip of the pressure nozzle 13a. Subsequently, the solid-phase extraction container 11 is pressurized. A liquid component Liq1a of the extraction material liquid Liq1 passes through the bottom filter F1 under pressure and is drained. The powder of the solid-phase extraction material M1, which has been dispersed in the extraction material liquid Liq1, remains over the bottom filter F1. That is, the solid-phase extraction material M1 is stopped by the bottom filter F1.

In the fifth step SA5 shown in FIG. 4E, the control unit 50 controls the extraction container table 12 to transfer the solid-phase extraction container 11 containing the solid-phase extraction material M1 directly under the filter supplying mechanism 14a. Next, the control unit 50 controls the filter supplying mechanism 14a to supply a filter (or top filter F2) to the body part 11a of the solid-phase extraction container 11. The top filter F2 stops at the interface between the diameter-reducing part 11c and the discharge passage 11b.

In the sixth step SA6 shown in FIG. 4F, the control unit 50 controls the extraction container table 12 to transfer the solid-phase extraction container 11 containing the top filter F2 directly under the determining mechanism 14b for filling position.

Next, the control unit 50 controls the determining mechanism 14b to determine the position of the top filter F2 in the same manner as in the case of determining the position of the bottom filter F1.

The top filter F2 that has been pushed into the discharge passage 11b by the rod 141 is stopped at a position where the solid-phase extraction material M1 is appropriately compressed.

In the seventh step SA7 shown in FIG. 4G, the control unit 50 detects a pressure imposed on the pressure sensor 140c by the rod 141. When this pressure reaches a predetermined value, the main body 140 is moved upward.

The top filter F2 still stays at the discharge passage 11b of the solid-phase extraction container 11, so that the position of the top filter F2 is determined.

In this way, in Embodiment 1, the determining mechanism 14b determines the position of the top filter F2, by which the position of the solid-phase extraction material M1 is determined. Accordingly, the solid-phase extraction container 11 is thus filled with the solid-phase extraction material M1. Hence, the filling mechanism for the solid-phase extraction material according to Embodiment 1 includes the supplying mechanism 14c for solid-phase extraction material and the determining mechanism 14b for filling position.

In view of the above, the step of filling a solid-phase extraction material includes the first step SA1 to the seventh step SA7. By using those steps, the discharge passage 11b of the solid-phase extraction container 11 is filled with the solid-phase extraction material M1 interposed between the bottom filter F1 and the top filter F2.

Note that FIGS. 4A to 4G illustrate the step of filling a solid-phase extraction material, in which the solid-phase extraction container 11 having the convex portion 11d with a triangular cross section is shown to be filled with the bottom filter F1, the solid-phase extraction material M1, and the top filter F2.

However, the step of filling a solid-phase extraction material as illustrated in FIGS. 4A to 4G can also be applied to the solid-phase extraction container 11 of which internal diameter inside the discharge passage 11b is gradually decreased from the body part 11a side as shown in FIG. 2B. Accordingly, this solid-phase extraction container 11 in FIG. 2B can also be filled with the bottom filter F1, the solid-phase extraction material M1, and the top filter F2.

If a diameter of the spherical bottom filter F1 is larger than the internal diameter R1 of the entry portion of the discharge passage 11b at the body part 11a side, as the bottom filter F1 moves along the internal surface of the discharge passage 11b of which internal diameter is decreased from the body part 11a side, resistance against the bottom filter F1 gradually increases. When this resistance becomes larger than the elastic force of the spring 142 (see FIG. 3) supporting the rod 141, the spring 142 is subjected to elastic compression and the forward movement of the bottom filter F1 is stopped. The determining mechanism 14b for filling position (see FIG. 3) sets the position of the bottom filter F1 at the position where the forward movement of the bottom filter F1 is stopped in the discharge passage 11b.

After that, the third step SA3 to the seventh step SA7 as illustrated in FIGS. 4A to 4G are executed. By doing so, the solid-phase extraction container 11 having a structure in which the internal diameter inside the discharge passage 11b is decreased from the body part 11a side can also be filled with the bottom filter F1, the solid-phase extraction material M1, and the top filter F2.

FIGS. 5A to 5C illustrate a solid-phase extraction step of subjecting a measurement component contained in a sample solution to solid-phase extraction in the solid-phase extraction container filled with the solid-phase extraction material. FIG. 5A shows an adsorption step. FIG. 5B shows a cleaning step. FIG. 5C shows an elution step. As shown in FIGS. 5A to 5C, the solid-phase extraction step uses three steps to subject the measurement component in the sample solution to solid-phase extraction, followed by purification. With reference to FIGS. 5A to 5C, the solid-phase extraction step will be described in detail (see FIGS. 1 to 3, if necessary).

In the adsorption step SB1 shown in FIG. 5A, the control unit 50 controls the sample transfer table 22 to transfer the sample container 21 under a first position of the sample dispensing mechanism 23. In the sample container, is dispersed the sample solution Liq2 in which the measurement component is dissolved. Next, the control unit 50 controls the sample dispensing mechanism 23 to suck the sample solution Liq2 in the sample container 21 by using the suction mechanism 23a1 of the sample dispensing arm 23a. Further, the control unit 50 controls the extraction container table 12 to transfer the solid-phase extraction container 11 containing the solid-phase extraction material M1 under a second position of the sample dispensing mechanism 23. Then, the sample dispensing arm23a used for sucking the sample solution Liq2 is moved to the second position for the solid-phase extraction container 11. After that, the sucked sample solution Liq2 is injected into the body part 11a of the solid-phase extraction container 11.

Further, the control unit 50 controls the extraction container table 12 to transfer the solid-phase extraction container 11 containing the sample solution Liq2 directly under the extraction processor 13. Thereafter, the control unit 50 controls the extraction processor 13 to fit the pressure nozzle 13a into the body part 11a of the solid-phase extraction container 11. Furthermore, the control unit 50 permits high-pressure air to be fed from the pressure nozzle 13a into the body part 11a of the solid-phase extraction container 11. Accordingly, the inside of the solid-phase extraction container 11 is pressurized. The sample solution Liq2 injected into the body part 11a passes through, in sequence, the top filter F2, the solid-phase extraction material M1, and the bottom filter F1. During this process, the measurement component contained in the sample solution Liq2 is adsorbed on the solid-phase extraction material M1. Meanwhile, a liquid component Liq2a of the sample solution Liq2 is discharged from the release hole 11b1.

In the cleaning step SB2 shown in FIG. 5B, the control unit 50 controls the extraction container table 12 to transfer the solid-phase extraction container 11 containing the solid-phase extraction material M1 having adsorbed thereon the measurement component under a first position of the reagent injection mechanism 16. Next, the control unit 50 controls the reagent injection mechanism 16 to suck the cleaning reagent Liq3 in the reagent container 31 by using the suction mechanism 16a1 and to inject the cleaning reagent Liq3 into the body part 11a of the solid-phase extraction container 11.

As described above, based on the reagent information and the positional information of the reagent container 31 on the reagent transfer table 32, the information being written in the computation system 45, the control unit 50 identifies the reagent container 31 containing the cleaning reagent Liq3. Then, the control unit 50 controls the reagent transfer table 32 to transfer the reagent container 31 containing the cleaning reagent Liq3 under a second position of the reagent injection mechanism 16.

Further, the control unit 50 controls the extraction container table 12 to transfer the solid-phase extraction container 11 containing the cleaning reagent Liq3 directly under the extraction processor 13. Thereafter, the control unit 50 controls the extraction processor 13 to fit the pressure nozzle 13a into the body part 11a of the solid-phase extraction container 11. Furthermore, the control unit 50 permits high-pressure air to be fed from the pressure nozzle 13a into the solid-phase extraction container 11. Accordingly, the inside of the solid-phase extraction container 11 is pressurized. When the cleaning reagent Liq3 passes through the solid-phase extraction material M1 and is discharged, impurities adsorbed on the solid-phase extraction material M1 having thereon the measurement component are discharged together with the cleaning reagent Liq3 from the release hole Hb1.

In the elution step SB3 shown in FIG. 5C, the control unit 50 controls the extraction container table 12 to transfer the solid-phase extraction container 11 after the cleaning step SB2 under the first position of the reagent injection mechanism 16. Next, the control unit 50 controls the reagent transfer table 32 to transfer the reagent container 31 containing the eluent Liq4a under the second position of the reagent injection mechanism 16.

As described above, based on the reagent information and the positional information of the reagent container 31 on the reagent transfer table 32, the information being written in the computation system 45, the control unit 50 identifies the reagent container 31 containing the eluent Liq4a. Then, the control unit 50 controls the reagent transfer table 32 to transfer the reagent container 31 containing the eluent Liq4a under the second position of the reagent injection mechanism 16.

Subsequently, the control unit 50 controls the reagent injection mechanism 16 to suck the eluent Liq4 added to the reagent container 31 by using the suction mechanism 16a1 of the reagent injection arm 16a and to inject the sucked eluent Liq4a into the body part 11a of the solid-phase extraction container 11.

After that, the control unit 50 controls the extraction container table 12 to transfer the solid-phase extraction container 11 containing the eluent Liq4 directly under the extraction processor 13. Further, the control unit 50 controls the eluate transfer table 42 to transfer the eluate storing container 41 directly under the solid-phase extraction container 11.

Furthermore, the control unit 50 controls the extraction processor 13 to fit the pressure nozzle 13a into the body part 11a of the solid-phase extraction container 11 and to permit high-pressure air to be fed from the pressure nozzle 13a into the solid-phase extraction container 11. Accordingly, the inside of the solid-phase extraction container 11 is pressurized. The eluent Liq4a passes through the top filter F2, the solid-phase extraction material M1, and the bottom filter F1, all of which have been set in the discharge passage 11b. Thereafter, the eluent Liq4a is pushed out from the release hole 11b1. When the eluent Liq4a passes through the solid-phase extraction material M1, the measurement component is eluted into the eluent Liq4a. Subsequently, an eluate Liq4b containing the measurement component is added dropwise to the eluate storing container 41, and the eluate storing container 41 finally receives the eluate Liq4b containing the measurement component.

In view of the above, the solid-phase extraction step includes the adsorption step SB1, the cleaning step SB2, and the elution step SB3. By using those steps, the measurement component is eluted from the solid-phase extraction container 11 and the eluate storing container 41 receives the eluate Liq4b containing the measurement component.

Thereafter, the control unit 50 controls the eluate transfer table 42 to transfer the eluate storing container 41 having the eluate Liq4b included during the solid-phase extraction step under a position of the liquid transfer unit 44 of the sample analyzing section 40. Then, the control unit 50 controls the liquid transfer unit 44 to send the eluate Liq4b contained in the eluate storing container 41 to the analyzing unit 43 and also controls the analyzing unit 43 to analyze the measurement component included in the eluate Liq4b.

At the same time, the control unit 50 executes the container cleaning step, and the solid-phase extraction container after the solid-phase extraction is washed.

FIGS. 6A to 6C illustrate the container cleaning step. FIG. 6A shows a preparatory step. FIG. 6B shows a pushing step. FIG. 6C shows a cleaning step.

As shown in FIGS. 6A to 6C, the container cleaning step includes three steps, and the solid-phase extraction container 11 is washed. With reference to FIGS. 6A to 6C, the container cleaning step will be described in detail (see FIGS. 1 to 3, if necessary).

In the preparatory step SC1 shown in FIG. 6A, the control unit 50 controls the extraction container table 12 to transfer the solid-phase extraction container 11 after the solid-phase extraction over the container cleaning mechanism 17.

The container cleaning mechanism 17 includes: a waste port 17b that vertically moves using a lift mechanism (not shown); and a waste container 17a that receives waste from the solid-phase extraction container 11.

The waste container 17a has an upper opening. This opening portion has a separation membrane 17a1 that can separate a solid from liquid. Then, the waste container 17a receives the waste that falls down from the release hole 11b1 of the solid-phase extraction container 11.

Accordingly, the container cleaning mechanism 17 is preferably disposed under the solid-phase extraction container 11 of the extraction container table 12 fixed to the analyzer 1.

Further, the container cleaning mechanism 17 has the waste port 17b that guides, into the waste container 17a, the waste falling through the release hole 11b1 of the solid-phase extraction container 11. The waste port 17b according to Embodiment 1 is a hollow pipe and is lifted to be fitted outside the discharge passage 11b of the solid-phase extraction container 11.

In addition, the waste container 17a is transferred under the solid-phase extraction container 11 by using a transfer mechanism (not shown) (e.g., a transfer table, a transfer arm).

In the preparatory step SC1, the control unit 50 controls the container cleaning mechanism 17 having the above structure to fit the waste port 17b outside the discharge passage 11b of the solid-phase extraction container 11 and to transfer the waste container 17a directly under the solid-phase extraction container 11.

In the pushing step SC2 shown in FIG. 6B, the control unit 50 controls a discharging mechanism 15 to eject the top filter F2, the solid-phase extraction material M1, and the bottom filter F1, all of which have been packed in the solid-phase extraction container 11.

The discharging mechanism 15 has a work arm 15a that rotates over the solid-phase extraction container 11 mounted on the extraction container table 12. In addition, the work arm 15a has a discharge rod 15b that can move vertically. The discharge rod 15b has a diameter smaller than the internal diameter inside the discharge passage 11b of the solid-phase extraction container 11. The discharge rod 15b has a function of moving downward into the discharge passage 11b to push and eject the top filter F2, the solid-phase extraction material M1, and the bottom filter F1 through the release hole 11b1.

Here, in the pushing step SC2, the control unit 50 controls the discharging mechanism 15 to transfer the work arm 15a over the solid-phase extraction container 11. Also, the discharge rod 15b is moved downward and is used to push and eject the top filter F2, the solid-phase extraction material M1, and the bottom filter F1 through the release hole 11b1 of the solid-phase extraction container 11.

As illustrated in the cleaning step SC3 of FIG. 6C, the top filter F2, the solid-phase extraction material M1, and the bottom filter F1 that have been ejected from the release hole 11b1 are guided to the waste port 17b and are put in the waste container 17a. At this time, the solid materials such as the top filter F2, solid-phase extraction material M1, and bottom filter F1 do not pass through the separation membrane 17a1 and are placed on the separation membrane 17a1.

Note that the structure of the discharging mechanism 15 is not limited to the above. For example, as an alternative for the discharge rod 15b, high-pressure air may be used to blow the air into the solid-phase extraction container 11. This high-pressure air may be used to discharge the top filter F2, the solid-phase extraction material M1, and the bottom filter F1 from the release hole 11b1.

In the cleaning step SC3, the control unit 50 controls the container cleaning mechanism 17 to wash the solid-phase extraction container 11.

For example, the container cleaning mechanism 17 includes a container cleaning arm 17c that injects a container cleaning liquid Liq5, such as methanol and ethanol, into the body part 11a of the solid-phase extraction container 11 from an upper side. The control unit 50 controls the container cleaning mechanism 17 to move the container cleaning arm 17c over the solid-phase extraction container 11.

Further, as shown in the left diagram of the cleaning step SC3, the container cleaning liquid Liq5 is injected from the container cleaning arm 17c into the body part 11a of the solid-phase extraction container 11 and is used to wash the solid-phase extraction container 11.

The container cleaning liquid Liq5, which has been used to wash the solid-phase extraction container 11, flows out from the release hole 11b1, passes through the waste port 17b, and flows into the waste container 17a. Furthermore, as shown in the right diagram of the cleaning step SC3, the liquid container cleaning liquid Liq5 passes through the separation membrane 17a1 and is stored below the separation membrane 17a1.

In this way, the waste container 17a makes it possible to separate the liquid container cleaning liquid Liq5 from the solid top filter F2, solid-phase extraction material M1, and bottom filter F1. Accordingly, both the liquid and the solids are separately stored.

Note that the analyzer 1 may include a discharging mechanism cleaning unit 18 that washes the discharge rod 15b of the work arm 15a. While the solid-phase extraction container 11 is washed, the control unit 50 commands the work arm 15a to move to a position of the discharging mechanism cleaning unit 18. Then, the discharge rod 15b is washed. Here, the structure of the discharging mechanism cleaning unit 18 is not limited to the above. For example, a cleaning solution for washing the rod 15b may be sprayed on the discharge rod 15b to be cleaned.

As described above, the analyzer 1 (see FIG. 1) according to Embodiment 1 appropriately executes the step of filing a solid-phase extraction material, the solid-phase extraction step, and the container cleaning step. During those steps, the analyzing unit 43 (see FIG. 1) determines the measurement component dissolved in the eluate Liq4b and the computation system 45 calculates the analysis results.

Figure 7:
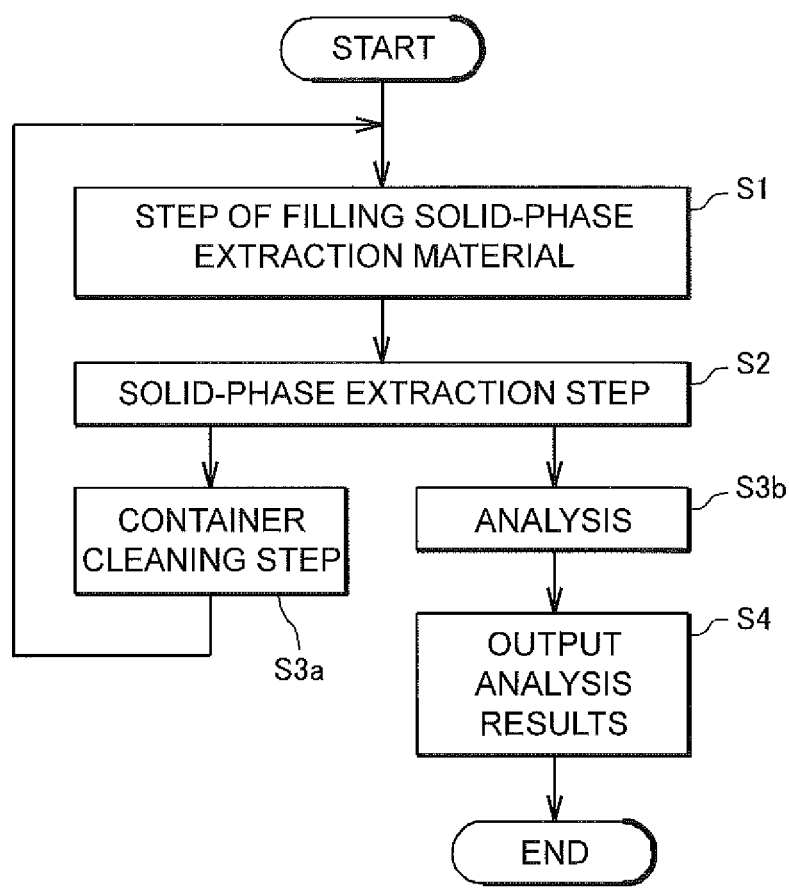
FIG. 7 is a flow chart illustrating how an analyzer analyzes a measurement component.

FIG. 7 is a flow chart illustrating how the analyzer analyzes the measurement component.

With reference to FIG. 7, a procedure how the analyzer 1 analyzes the measurement component dissolved in the eluate Liq4b will be described in detail (see FIGS. 1 to 5C, as needed).

For example, when a user starts operating the analyzer 1, the control unit 50 executes the step of filing a solid-phase extraction material (Step S1) as illustrated in FIGS. 4A to 4G. Next, the control unit 50 executes the solid-phase extraction step (Step S2) as illustrated in FIGS. 5A to 5C by using the solid-phase extraction container 11 filled with the solid-phase extraction material M1 interposed between the bottom filter F1 and the top filter F2.

Once the eluate storing container 41 receives the eluate Liq4b containing the measurement component of analytical target by executing the solid-phase extraction step (Step S2), the control unit 50 executes the container cleaning step (Step S3a) as illustrated in FIGS. 6A to 6C so as to wash the solid-phase extraction container 11 that has been used for the solid-phase extraction. Then, in order to refill the cleaned solid-phase extraction container 11 with the solid-phase extraction material M1, the step of filing a solid-phase extraction material (Step S1) is executed. That is, the control unit 50 returns the process to Step S1.

In addition, the control unit 50 executes analysis (Step S3b) of the measurement component dissolved in the eluate Liq4b while executing the container cleaning step (Step S3a). Specifically, the control unit 50 makes the liquid transfer unit 44 send the eluate Liq4b containing the measurement component, the eluate having been stored in the eluate storing container 41, to the analyzing unit 43 to determine the measurement component and to obtain a measured value. Further, the control unit 50 controls the analyzing unit 43 to input the measured value into the computation system 45. Furthermore, the control unit 50 commands the computation system 45 to calculate the analysis results based on the input measured value.

After that, the control unit 50 commands the computation system 45 to input the calculated analysis results into the external communication interface 45a. In addition, the control unit 50 controls the external communication interface 45a to output the analysis results on a monitor and/or a printer (not shown) (Step S4).

The analyzer 1 appropriately executes, for example, the step of filing a solid-phase extraction material, the solid-phase extraction step, and the container cleaning step in the process indicated in FIG. 7, thereby analyzing the measurement component contained in the sample solution Liq2 (see FIG. 5A). At this time, the control unit 50 simultaneously executes the container cleaning step (Step S3a) and the analysis (Step S3b) of the measurement component in the analyzing unit 43 and the computation system 45.

In view of the above, the analyzer 1 (see FIG. 1) according to Embodiment 1 includes: the solid-phase extraction container 11 (see FIG. 1) that can be filled with the solid-phase extraction material M1 (see FIG. 4C); and the filling mechanism 14 (see FIG. 1) for solid-phase extraction material, the mechanism 14 being used to fill the solid-phase extraction container 11 with the solid-phase extraction material M1.

In addition, the solid-phase extraction material M1 packed in the solid-phase extraction container 11 can be discharged. Accordingly, the analyzer 1 has the discharging mechanism 15 (see FIG. 1) for discharging the solid-phase extraction material M1 from the solid-phase extraction container 11.

According to this configuration, the solid-phase extraction material M1 can be discharged from the solid-phase extraction container 11 after the measurement component is subjected to the solid-phase extraction. Then, the solid-phase extraction material M1 can be disposed of. In addition, the solid-phase extraction container 11 free of the solid-phase extraction material M1 can be refilled with a new solid-phase extraction material M1. Hence, the solid-phase extraction container 11 can be recycled, so that its disposal is unnecessary and an amount of waste generated can be decreased. Further, the waste generated is the filters (i.e., the bottom filter F1 and the top filter F2) and the solid-phase extraction material M1. This makes it possible to reduce the amount of waste generated.

Moreover, recycling the solid-phase extraction container 11 also makes it possible to reduce a replacement cost for the solid-phase extraction container 11. Collectively, a running cost for the analyzer 1 can be minimized.

Note that the number of recycling times and/or the used hours may be limited regarding the solid-phase extraction container 11 shown in FIG. 1. In these cases, the computation system 45 may determine a replacement time for the solid-phase extraction container 11.

For example, the control unit 50 permits a predetermined reagent (e.g., a reagent for the analyzer: a calibrator) to be regularly used for solid-phase extraction in the solid-phase extraction container 11. Then, the analyzing unit 43 measures the reagent to obtain a measured value. Examples of the reagent that can be used include, but are not limited to, organic solvents such as methanol.

Further, the control unit 50 controls the analyzing unit 43 to input the obtained measured value into the computation system 45. After that, the control unit 50 commands the computation system 45 to calculate the analysis results based on the measured value of the reagent for the analyzer, which measured value has been input from the analyzing unit 43. Afterwards, the analysis results are stored in a storage medium (not shown). Then, a difference between these analysis results and the analysis results obtained just after the replacement of the solid-phase extraction container 11 is determined. A state where the difference exceeds a predetermined value (e.g., 20%) may occur the predetermined number of times or more. In this case, the computation system 45 determines that the solid-phase extraction container 11 used for the solid-phase extraction of the reagent for the analyzer reaches a usage limit. Consequently, an alert indicating the replacement time for the solid-phase extraction container 11 should be output.

In addition, the computation system 45 may count the number of solid-phase extraction times per solid-phase extraction container 11. When the count exceeds a predetermined number, the computation system 45 may output an alert indicating the replacement time for the solid-phase extraction container 11.

In addition, the computation system 45 may determine a type of reagent used and/or a kind of measurement component for each solid-phase extraction container 11 and/or may count the numbers of usage times for the reagent used and/or each measurement component. When the count exceeds a predetermined number for the reagent and/or each measurement component, the computation system 45 may output an alert indicating the replacement time for the solid-phase extraction container 11.

Further, the alert output from the computation system 45 may be sent via the external communication interface 45a to a personal computer (not shown), etc. Also, the personal computer may display the position of the solid-phase extraction container 11 that is subject to the alert. In this case, a user of the analyzer 1 can easily specify which solid-phase extraction container 11 should be replaced.

In addition, the control unit 50 may execute the solid-phase extraction step without using the solid-phase extraction container 11 that is subject to the alert.

Note that how the computation system 45 determines which solid-phase extraction container 11 should be replaced is not limited to the above-described method.

Modification Embodiment 1

For example, modification embodiments of the solid-phase extraction container 11 seem to fall under Modification Embodiment 1 according to Embodiment 1.

FIGS. 8A and 9C illustrate modification embodiments of the solid-phase extraction container. FIG. 8A is a cross-sectional view illustrating that a cross section shape has a semicircular convex portion. FIG. 8B is a cross-sectional view illustrating that a cross section shape has a rectangular convex portion. FIG. 8C is a cross-sectional view illustrating that a cross section shape has a concave portion. FIG. 8D is a cross-sectional view illustrating that a cross section shape has a triangular concave portion. FIG. 8E is a cross-sectional view illustrating that a cross section shape has a semicircular concave portion. In addition, FIG. 9A is a cross-sectional view illustrating a shape where the periphery of a release hole is tilted toward both opposing ends. FIG. 9B is a cross-sectional view illustrating a shape where the periphery of a release hole is chamfered. FIG. 9C is a cross-sectional view illustrating a shape where the periphery of a release hole is tilted from one end to the other opposing end.

As shown in FIG. 2A, in Embodiment 1, the discharge passage 11b of the solid-phase extraction container 11 has a convex portion 11d with a triangular cross section shape.

The cross section shape of the convex portion 11d, however, is not limited to the triangular shape. For example, as shown in FIG. 8A, the convex portion 11d1 having a semicircular cross section shape (or a part of an arc) may be allowed. As shown in FIG. 8A, the convex portion 11d2 having a rectangular cross section shape may also be allowed. As for the convex portion 11d2 having a rectangular cross section shape, its corners may be chamfered by 0.1 mm or greater.

Note that in the cases of the convex portion 11d1 with a semicircular cross section shape and the convex portion 11d2 with a rectangular cross section shape, the height Ht of protrusion from the internal surface of the discharge passage 11b is preferably set to be within a range of "0.1 (mm) ≤Ht≤0.2×R1 (mm)". Also note that the "R1" represents an internal diameter of the discharge passage 11b at the body part 11a side (see FIG. 2A) (hereinafter, the same applies to the following).

In addition, as shown in FIG. 8C, the internal surface of the discharge passage 11b may have the concave portion 11e that is grooved all around the circumference.

If the grooved concave portion 11e is created in the discharge passage 11b, the forward movement of the bottom filter F1 is prevented because the bottom filter F1 pushed into the discharge passage 11b expands at the position of the concave portion 11e. This generates resistance force to prevent the bottom filter F1-pushing rod 141 (see FIG. 3) from traveling further into the discharge passage 11b. Then, the determining mechanism 14b for filling position (see FIG. 3) sets the position of the concave portion 11e to the position of the bottom filter F1 at the discharge passage 11b. In this way, the concave portion 11e, which is formed on the internal surface of the discharge passage 11b, has a function equivalent to that of the convex portion 11d (see FIG. 2A). Note that the depth Dp of the concave portion 11e formed on the discharge passage 11b is preferably set to be within a range of "0.1 (mm)≤Dp≤0.2×R1 (mm)" when the depth from the internal surface is measured.

In addition, the cross section shape of the concave portion 11e is not limited to a rectangular shape. As shown in FIG. 8D, the concave portion 11e1 with a triangular cross section shape may be allowed. As shown in FIG. 8E, the concave portion 11e2 with a semicircular cross section shape (or a part of an arc) may also be allowed.

The depth Dp of the concave portion 11e1 with a triangular cross section shape or the concave portion 11e2 with a semicircular cross section shape is also preferably set to be within a range of "0.1 (mm)≤Dp≤0.2×R1 (mm)" when the depth from the internal surface is measured.

Also, the concave portion 11e1 with a triangular cross section shape preferably has an inner surface angle θ2 of 0.1 degree or more when viewed from the top.

In addition, the shape surrounding the release hole 11b1 of the solid-phase extraction container 11 is not limited.

For example, as shown in FIG. 9A, the shape may be inclined from the release hole 11b1 toward both opposing ends. In this case, the inclination angle θ3 is preferably set to be within a range of "0.1 (degree)≤θ3≤90 (degrees)". In addition, as shown in FIG. 9B, the surrounding of the release hole 11b1 may be chamfered. In this case, the chamfer angle θ4 is preferably set to be within a range of "0.1 (degree) ≤θ4≤90 (degrees)". In addition, the shape (not shown) may be chamfered like an R-shape. In addition, as shown in FIG. 9C, the shape may be inclined from one end toward the opposing end. In this case, the inclination angle θ5 is preferably set to be within a range of "0.1 (degree)≤θ5≤90 (degrees)".

In addition, examples of the shape (not shown) may include different shapes. Overall, the shape surrounding the release hole 11b1 of the solid-phase extraction container 11 (see FIG. 1) is not limited.

Modification Embodiment 2

For example, modification embodiments of the extraction container table 12 seem to fall under Modification Embodiment 2 according to Embodiment 1.

Figure 10:
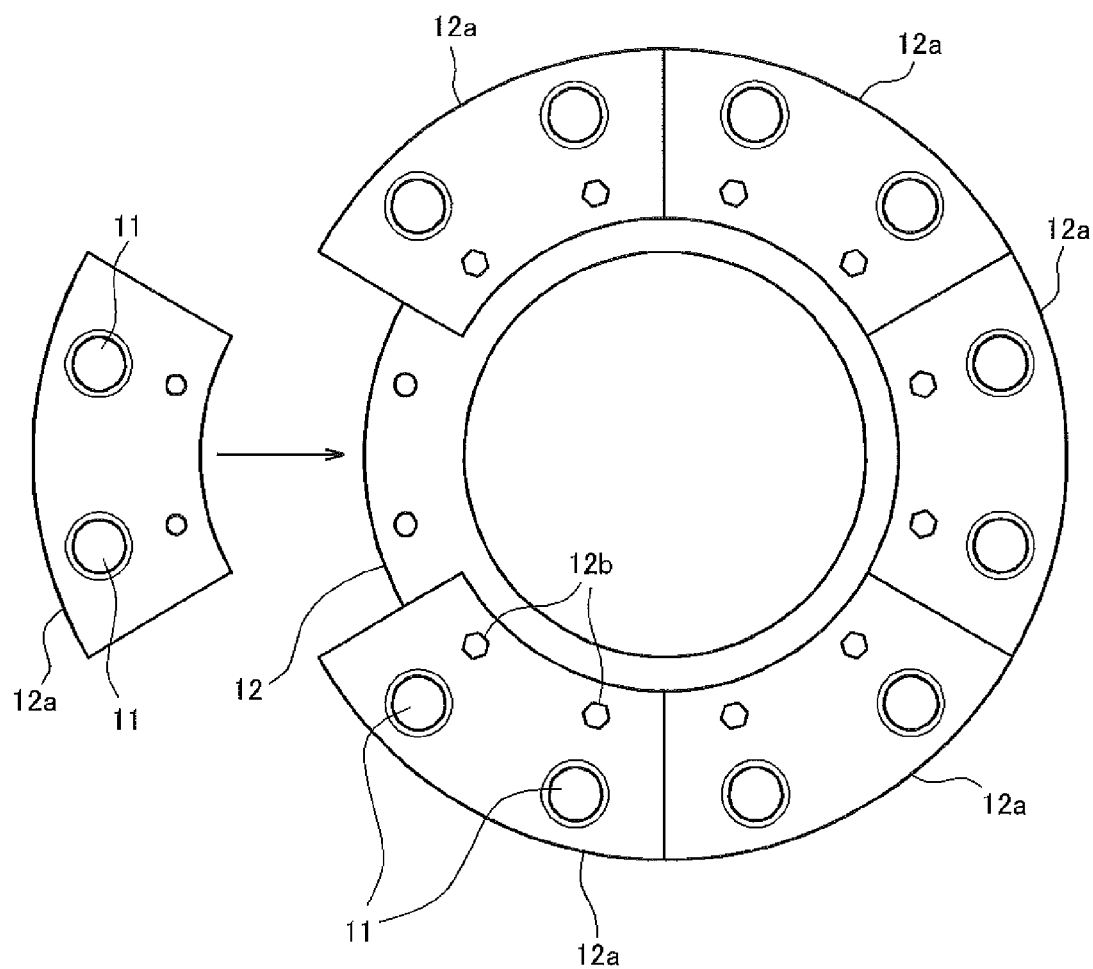
FIG. 10 illustrates an extraction container table including detachable bases.

FIG. 10 illustrates a modification embodiment of the extraction container table.

In Embodiment 1, the solid-phase extraction containers 11 (see FIG. 1) are installed on the extraction container table 12 (see FIG. 1). In this case, the solid-phase extraction containers 11 may be replaced with the whole extraction container table 12.

The extraction container table 12, however, is not limited to this configuration.

For example, as shown in FIG. 10, the surrounding of the extraction container table 12 may have a plurality of detachable bases 12a (e.g., 6 bases in FIG. 10) each having mounted thereon one or more solid-phase extraction containers 11 (e.g., 2 containers in FIG. 10).

According to this structure, the solid-phase extraction containers 11 are integrated into the detachable base 12a, and each complex is detachable on the extraction container table 12. For example, there may be some usable and some unusable solid-phase extraction containers 11 on the extraction container table 12. In such a case, the detachable base 12a having any unusable solid-phase extraction container 11 may be replaced. This makes the replacement of the whole extraction container table 12 unnecessary and enables the usable solid-phase extraction containers to be used continually. Hence, the above can reduce disposal of the usable solid-phase extraction containers 11, thereby suitably decreasing an amount of waste generated.

Note that how the detachable bases 12a are mounted on the extraction container table 12 is not limited. For example, a fastener member 12b such as a bolt may be used to fix each detachable base 12a to the extraction container table 12.

In addition, the number (6 bases) of detachable bases 12a attached to the extraction container table 12 and/or the number (2 containers) of solid-phase extraction containers 11 fixed to each detachable base 12a are presented as an example. The numbers are thus not limited to the above numbers. For example, a large analyzer 1 may have an extraction container table 12 having attached thereon detachable bases 12a holding about 50 solid-phase extraction containers 11.

Embodiment 2

Figure 11:
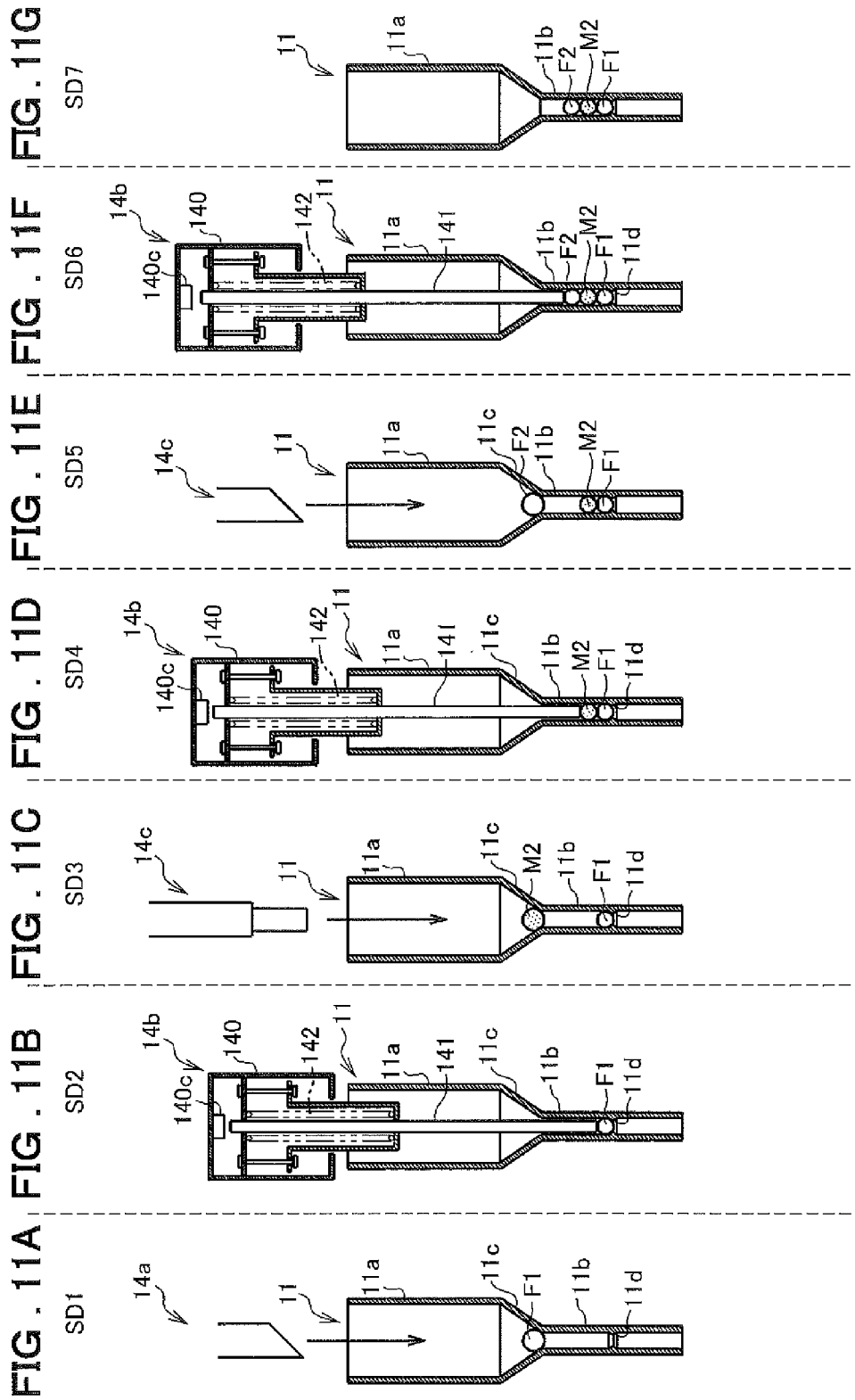
FIGS. 11A to 11G illustrate a step of filling a solid-phase extraction material. Herein, a solid-phase extraction container is filled with a monolithic solid-phase extraction material.

In Embodiment 2, instead of using the solid-phase extraction material M1 powder (see FIG. 4C), the solid-phase extraction container 11 is filled with a monolithic (solidified) solid-phase extraction material M2 as shown in FIG. 11.

The analyzer 1 (see FIG. 1) of Embodiment 2 has the same structure as of Embodiment 1, but the step of filing a solid-phase extraction material differs from that of Embodiment 1. With reference to FIG. 11, the following describes the step of filing a solid-phase extraction material according to Embodiment 2 (see FIGS. 1 to 3, if necessary).

The step of filling the solid-phase extraction container 11 with the monolithic solid-phase extraction material M2 includes 7 steps (the first step SD1 to seventh step SD7) as illustrated in FIGS. 11A to 11G.

The first step SD1 shown in FIG. 11A and the second step SD2 shown in FIG. 11B are equivalent to the first step SA1 and the second step SA2 (see FIGS. 4A to 4G) in the step of filing a solid-phase extraction material according to Embodiment 1. The second step SD2 is executed to fill the bottom filter F1 into the discharge passage 11b of the solid-phase extraction container 11.

In the third step SD3 shown in FIG. 11C, the control unit 50 controls the extraction container table 12 to transfer the solid-phase extraction container 11 containing the bottom filter F1 directly under the supplying mechanism 14c for solid-phase extraction material.

Next, the control unit 50 controls the supplying mechanism 14c to throw the monolithic solid-phase extraction material M2 in the body part 11a of the solid-phase extraction container 11. The supplying mechanism 14c according to Embodiment 2 causing, for example, a spherical, monolithic solid-phase extraction material M2 to fall down in the solid-phase extraction container 11. Preferably, the solid-phase extraction material M2 has a diameter larger than the internal surface diameter of the discharge passage 11b. This configuration makes the solid-phase extraction material M2 stop at the interface between the diameter-reducing part 11c and the discharge passage 11b.

Note that the shape of the monolithic solid-phase extraction material M2 is not limited to a sphere. A cylindrical or conical solid-phase extraction material M2 may be allowed. Also, a cylindrical material M2 with a taper or a step may be allowed. In addition, examples of its cross section shape include polygonal shapes such as square, rectangular, trapezoidal, and rhombic, shapes.

In the fourth step SD4 shown in FIG. 11D, the control unit 50 controls the extraction container table 12 to transfer the solid-phase extraction container 11 containing the solid-phase extraction material M2 directly under the determining mechanism 14b for filling position.

In addition, the control unit 50 moves the main body 140 of the determining mechanism 14b downward. The rod 141 is made to enter the solid-phase extraction container 11 containing the solid-phase extraction material M2. The rod 141 further enters the discharge passage 11b while pushing forward the solid-phase extraction material M2 into the discharge passage 11b.

When the solid-phase extraction material M2 encounters the bottom filter F1, the material movement is prevented. At that time, upward resistance force is generated at the terminal of the rod 141. This resistance force involves subjecting the rod 141-supporting spring 142 to elastic compression, thereby stopping the forward movement of the rod 141. That is, the solid-phase extraction material M2 is locked by the bottom filter F1.

In addition, the spring 142 is subjected to elastic compression to regulate the solid-phase extraction material M2-pushing force of the rod 141.

The main body 140 may move downward while the rod 141 stops its forward movement. In this case, the rod 141 moves upward relative to the main body 140, and another terminal of the rod is in contact with the pressure sensor 140c. The pressure sensor 140c sends to the control unit 50 a detection signal generated when this terminal of the rod pressurizes the sensor. The control unit 50 receives the input detection signal sent from the pressure sensor 140c and can thereby detect a pressure generated by the rod 141 while the rod 141 is in contact with the pressure sensor 140c. When this pressure reaches a predetermined value, the main body 140 is made to move upward so as to dislocate the main body 140 from the solid-phase extraction container 11.

The solid-phase extraction material M2 still stays at the discharge passage 11b of the solid-phase extraction container 11, so that the position of the solid-phase extraction material M2 is determined.

The fifth step SD5 shown in FIG. 11E to the seventh step SD7 shown in FIG. 11G are substantially the same as the fifth step SA5 to the seventh step SA7 (see FIGS. 4A to 4G) in the step of filing a solid-phase extraction material according to Embodiment 1.

That is, in the fifth step SD5, the top filter F2 is supplied to the solid-phase extraction container 11 containing the solid-phase extraction material M2. In addition, in the sixth step SD6, the rod 141 of the determining mechanism 14b pushes the top filter F2 to a position in contact with the solid-phase extraction material M2, so that the position is determined. In the seventh step SD7, the monolithic solid-phase extraction material M2 interposed between the bottom filter F1 and the top filter F2 is packed in the discharge passage 11b of the solid-phase extraction container 11.

As described above, in the analyzer 1, not only the solid-phase extraction material M1 powder (see FIG. 4C), but also the monolithic solid-phase extraction material M2 can be packed in the solid-phase extraction container 11.

Note that a solid-phase extraction step and container cleaning step according to Embodiment 2 may be the same as the solid-phase extraction step (see FIG. 5) and container cleaning step (see FIG. 6) according to Embodiment 1.

According to Embodiment 2, the monolithic solid-phase extraction material M2 can be discharged from the solid-phase extraction container 11 after the measurement component contained in the sample solution Liq2 (see FIG. 5A) is subjected to the solid-phase extraction. Then, the monolithic solid-phase extraction material M2 can be disposed of. In addition, the solid-phase extraction container 11 free of the solid-phase extraction material M2 can be refilled with a new solid-phase extraction material M2. Hence, the solid-phase extraction container 11 can be recycled in a manner similar to that of Embodiment 1, so that the amount of waste generated can be decreased. Further, the running cost of the analyzer 1 can be much reduced. Moreover, the monolithic solid-phase extraction material M2 can also be utilized, which extends the utility of the analyzer 1.

Embodiment 3

Figure 12:
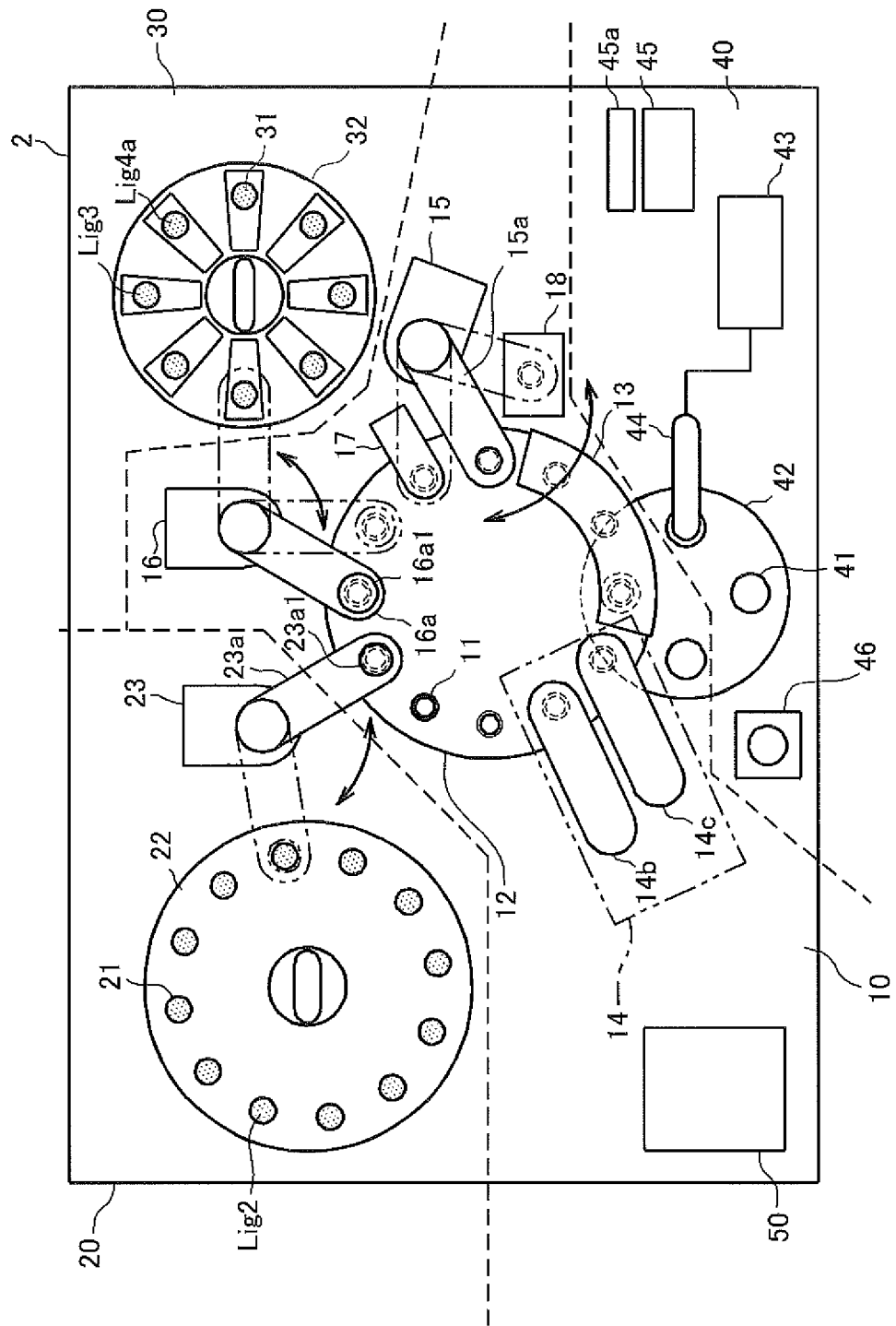
FIG. 12 illustrates how to configure an analyzer according to Embodiment 3.
Figure 13A:
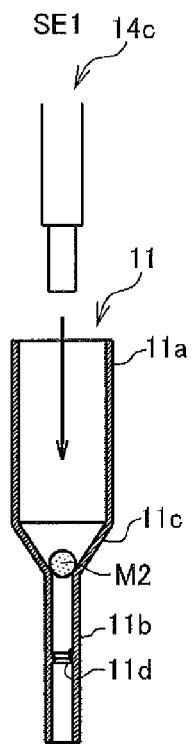
FIGS. 13A to 13C illustrate a step of filling a solid-phase extraction material according to Embodiment 3.
Figure 13B:
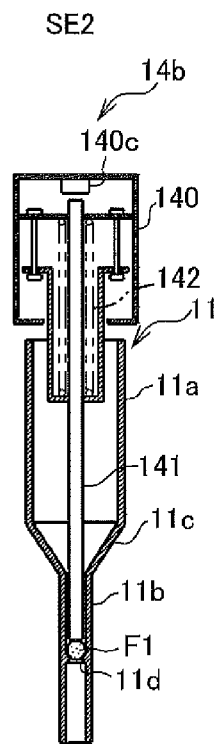
Figure 13C:
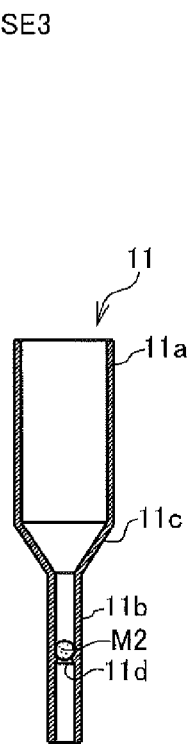

FIG. 12 illustrates how to configure an analyzer according to Embodiment 3. In addition, FIGS. 13A to 13C illustrate a step of filing a solid-phase extraction material according to Embodiment 3. FIG. 13A shows the first step. FIG. 13B shows the second step. FIG. 13C shows the third step.

Meanwhile, the solid-phase extraction material M2 according to Embodiment 2 is a monolithic and, for example, a mesh-like solid. Accordingly, in Embodiment 3, neither the top filter F2 nor the bottom filter F1 as shown in FIGS. 11A to 11G may be used for the filling.

Because of this, as shown in FIG. 12, an analyzer 2 may include no filter supplying mechanism 14a in the filling mechanism 14 (see FIG. 1) for solid-phase extraction material. Note that the analyzer 2 shown in FIG. 12 has the same structure as of the analyzer 1 shown in FIG. 1 except that no filter supplying mechanism 14*a* is provided.

In addition, the step of filling the solid-phase extraction container 11 with the solid-phase extraction material M2 according to Embodiment 3 includes three steps (the first step SE1 to third step SE3) as illustrated in FIGS. 13A to 13C.

In the first step SE1 shown in FIG. 13A, the control unit 50 (see FIG. 12) controls the extraction container table 12 (see FIG. 12) to transfer the solid-phase extraction container 11 directly under the supplying mechanism 14*c* for solid-phase extraction material.

Next, the control unit 50 controls the supplying mechanism 14*c* to throw the monolithic solid-phase extraction material M2 in the body part 11*a* of the solid-phase extraction container 11. Then, the solid-phase extraction material M2 stops at the interface between the diameter-reducing part 11*c* and the discharge passage 11*b*.

In the second step SE2 shown in FIG. 13B, the control unit 50 (see FIG. 12) controls the extraction container table 12 (see FIG. 12) to transfer the solid-phase extraction container 11 containing the solid-phase extraction material M2 directly under the determining mechanism 14*b* for filling position.

In addition, the control unit 50 moves the main body 140 of the determining mechanism 14*b* downward. The rod 141 is made to enter the solid-phase extraction container 11 containing the solid-phase extraction material M2. The rod 141 further enters the discharge passage 11*b* while pushing forward the solid-phase extraction material M2 into the discharge passage 11*b*.

When the solid-phase extraction material M2 encounters the convex portion 11*d* formed on the discharge passage 11*b*, the material movement is prevented. At that time, upward resistance force is generated at the terminal of the rod 141. This resistance force involves subjecting the rod 141-supporting spring 142 to elastic compression, thereby stopping the forward movement of the rod 141.

The spring 142 according to Embodiment 3 applies elastic force to the rod 141 in a traveling direction of the rod 141. Then, the rod 141 moves the solid-phase extraction material M2 along the inside of the discharge passage 11*b* by the elastic force applied by the spring 142

In addition, the spring 142 is subjected to elastic compression to regulate the solid-phase extraction material M2-pushing force of the rod 141, which keeps excessive pressure from being imposed on the solid-phase extraction material M2. Consequently, the above prevents the solid-phase extraction material M2 from being subject to plastic deformation.

In other words, it is preferable that the spring 142 according to Embodiment 3 applies elastic force to the rod 141 at a degree not to subject the solid-phase extraction material M2 to plastic deformation.

Specifically, the spring 142 preferably has smaller elastic force than the solid-phase extraction material M2.

According to this configuration, the solid-phase extraction material M2 is not subject to plastic deformation and the rod 141 can make the solid-phase extraction material M2 move along the internal surface of the discharge passage 11*b*.

The main body 140 may move downward while the rod 141 stops its forward movement. In this case, the rod 141 moves upward relative to the main body, and another terminal of the rod is in contact with the pressure sensor 140*c*. The pressure sensor 140*c* sends to the control unit 50 a detection signal generated when this terminal of the rod pressurizes the sensor. That is, the pressure sensor 140*c* according to Embodiment 3 is a pressure detection unit that detects, as a pressure, the force given to the rod 141 by the solid-phase extraction material M2 locked at the convex portion 11*d* of the discharge passage 11*b*.

In the third step SE3 shown in FIG. 13C, the control unit 50 (see FIG. 1) uses the detection signal input from the pressure sensor 140*c* to detect a pressure imposed on the pressure sensor 140*c* by the rod 141. When this pressure reaches a predetermined value, the main body 140 is moved upward so as to dislocate it from the solid-phase extraction container 11.

The solid-phase extraction material M2 is locked at the convex portion 11*d* and thus stays at the discharge passage 11*b* of the solid-phase extraction container 11. That is, the position of the convex portion 11*d* is determined to be the position of the solid-phase extraction material M2 at the discharge passage 11*b*. Then, the solid-phase extraction material M2 is packed in the solid-phase extraction container 11.

In this way, neither the top filter F2 nor the bottom filter F1 as shown in FIGS. 11A to 11G may not be packed in the solid-phase extraction container 11. This configuration needs no filter supplying mechanism 14*a*, so that a manufacturing cost for the analyzer 2 can be much reduced. In addition, a maintenance cost for the analyzer 2 is decreased by an amount of cost required for the filter supplying mechanism 14*a*, so that a running cost for the analyzer 2 can be decreased.

Further, the step of filling the solid-phase extraction container 11 with the solid-phase extraction material M2 has a less number of steps. Hence, the solid-phase extraction container 11 is more efficiently filled with the solid-phase extraction material M2.

Furthermore, only the solid-phase extraction material M2 is disposed of from the solid-phase extraction container 11 after the measurement component is subjected to the solid-phase extraction. Hence, the amount of waste generated can be effectively reduced.

Moreover, the cost for the filters can be cut and the running cost for the analyzer 2 can thus be decreased.

Note that a solid-phase extraction step and container cleaning step according to Embodiment 3 may be the same as the solid-phase extraction step (see FIGS. 5A to 5C) and container cleaning step (see FIGS. 6A to 6C) according to Embodiment 1.

In this way, neither the top filter F2 (see FIG. 11E) nor the bottom filter F1 (see FIG. 11A) may be required for the analyzer 2 (see FIG. 12) in which the solid-phase extraction container 11 is filled with the monolithic solid-phase extraction material M2. Overall, this embodiment can effectively reduce the running cost and the amount of waste generated.

Note that the present invention is not limited to the above embodiments and their modification embodiments. For example, the above embodiments detail the present invention for clarity purposes. The present invention is therefore not necessarily limited to embodiments having all the elements as described above.

In addition, parts of elements of one embodiment can be replaced by those in another embodiment. Further, elements of one embodiment can be added to those in another embodiment.

For example, as shown in FIG. 3, the determining mechanism 14*b* for filling position according to Embodiments 1 to 3 has the pressure sensor 140*c*. In the step of filing a solid-phase extraction material, the control unit 50 (see FIG. 1) controls the determining mechanism 14*b* depending on the pressure imposed on the pressure sensor 140c by the rod 141. The present invention, however, is not limited to this configuration.

For example, a sensor (not shown) that detects an amount of movement of the rod 141 may be used as an alternative for the pressure sensor 140c. In the step of filing a solid-phase extraction material, the control unit 50 may control the determining mechanism 14b depending on the amount of movement of the rod 141.

For example, in the step of filing a solid-phase extraction material as shown in FIG. 4, the bottom filter F1 may be in contact with the convex portion 11d of the solid-phase extraction container 11. In this case, the rod 141 moves upward relative to the main body 140 of the determining mechanism 14b. When the amount of movement of the rod 141 relative to the main body 140 reaches a predetermined value, the control unit 50 may move the determining mechanism 14b upward.

Alternatively, a sensor (not shown) may be used to detect, as an amount of progression (amount of movement) of the rod 141, an amount of progression (amount of movement) of the bottom filter F1 from the interface between the diameter-reducing part 11c and the discharge passage 11b. When this detection value reaches a predetermined value, the control unit 50 may move the determining mechanism 14b upward.

In addition, the discharge passage 11b (see FIG. 4A) of the solid-phase extraction container 11 may be irradiated with laser beams, and a laser sensor (not shown) may be used to detect the laser beams that penetrate through the discharge passage 11b. In this case, the laser sensor may detect a state that the laser beams are blocked by the bottom filter F1 (see FIG. 4A) or the top filter F2 (see FIG. 4E). At that time, the control unit 50 may move the determining mechanism 14b upward.

In addition, Embodiments 1 to 3 include the discharging mechanism 15 (see FIG. 1) for discharging, from the solid-phase extraction container 11 (see FIG. 1), the solid-phase extraction material M1 (see FIG. 6A), the top filter F2 (see FIG. 6A), the bottom filter F1 (see FIG. 6A), and the monolithic solid-phase extraction material M2 (see FIG. 11C). However, the rod 141 (see FIG. 3) of the determining mechanism 14b for filling position, for example, may be used to push the solid-phase extraction material M1, the top filter F2, the bottom filter F1, and the monolithic solid-phase extraction material M2 outside the solid-phase extraction container 11. This configuration needs no discharging mechanism 15, thereby capable of exerting an effect of decreasing a cost of manufacturing the analyzer 1 (see FIG. 1).

In addition, the convex portion 11d (see FIG. 2A) of the solid-phase extraction container 11 is created all around the internal surface of the discharge passage 11b in a circumference direction. The present invention is not limited to this shape. For example, the internal surface of the discharge passage 11b may have dot-like convex portions (not shown) in a circumferential direction. Specifically, the convex portion 11d may not extend all around the circumference, but the convex portion 11d may be appropriately segmentalized.

In addition, the spring 142 (see FIG. 3) is not limited to a compression spring, but may be a tension spring. Also, instead of using the spring 142, gas such as compressed air and/or liquid such as oil may be used to impart elastic force to the rod 141 (see FIG. 3).

In addition, the mechanisms for transferring the sample container 21 (see FIG. 1), the reagent container 31 (see FIG. 1), and/or the eluate storing container 41 (see FIG. 1) are not limited to the disk-shaped sample transfer table 22 (see FIG. 1), the reagent transfer table 32 (see FIG. 1), and/or the eluate transfer table 42 (see FIG. 1).

For example, the sample containers 21, the reagent containers 31, and/or the eluate storing containers 41 may be arranged like a grid with predetermined spacing and may be transferred using a transfer arm (not shown), etc.

In addition, the above-described laser sensor may be used to determine a position of the filter (e.g., the bottom filter F1 (see FIG. 4A)). In this case, the solid-phase extraction container 11 (see FIG. 2A) may have neither the convex portion 11d (see FIG. 2A) nor the concave portion 11e (see FIG. 8C) on the discharge passage 11b (see FIG. 2A).

In this case, it is preferable that the diameter of the filter and the internal diameter (R1) of the discharge passage 11b at the body part 11a side (see FIG. 2A) should be determined so as to satisfy a relationship: "pressure imposed on the filter during solid-phase extraction≤force imposed on the solid-phase extraction container 11 from the filter in the discharge passage 11b".

Note that the present invention is not limited to the above embodiments, and may be appropriately modified within an extent not departing from the scope of the present invention.

REFERENCE SIGNS LIST

1 Analyzer
11 Solid-phase extraction container (or Container)
11a Body part
11b Discharge passage
11b1 Release hole
11d Convex portion
11e Concave portion
14a Filter supplying mechanism (or Filling mechanism for filter)
14b Determining mechanism for filling position (Filling mechanism for a filter, filling mechanism for a solid-phase extraction material)
14c Supplying mechanism for a solid-phase extraction material (or Filling mechanism for a solid-phase extraction material)
17 Container cleaning mechanism
17a Waste container
17b Waste port
140c Pressure sensor (or Pressure detection unit)
141 Rod
142 Spring (or Elastic member)
F1 Bottom filter (Filter)
F2 Top filter (Filter)
M1 Solid-phase extraction material
M2 Solid-phase extraction material (or Monolithic solid-phase extraction material)

The invention claimed is:
1. An analyzer comprising:
  a container including:
    a body part to receive a sample solution, the sample solution containing a measurement component of analytical target; and
    a discharge passage to discharge the sample solution introduced from the body part;
  a filling mechanism for a solid-phase extraction material, the filling mechanism being configured to fill the discharge passage with the solid-phase extraction material for solid-phase extraction of the measurement component;

a discharging mechanism for discharging the solid-phase extraction material from the container after the measurement component is subjected to the solid-phase extraction;

a container cleaning mechanism for cleaning the container from which the solid-phase extraction material is removed; and the filling mechanism including a filter supplying mechanism for filling the discharge passage with a filter, wherein the discharging mechanism is configured to discharge the filter packed in the discharge passage as well as the solid-phase extraction material packed in the discharge passage;

an inside of the discharge passage has a convex or concave portion;

the filter is locked at the convex or concave portion;

the filter locked at the convex or concave portion locks the solid-phase extraction material, so that the discharge passage is filled with the filter and the solid-phase extraction material; and the filling mechanism for the solid-phase extraction material includes a determining mechanism for filling position, the determining mechanism setting a position of the filter in the discharge passage at a position of the convex or concave portion.

2. The analyzer according to claim 1, wherein the discharging mechanism is configured to discharge at least one of the solid-phase extraction material and the filter from a release hole formed at an end of the discharge passage.

3. The analyzer according to claim 2, further comprising:
a waste container to receive the solid-phase extraction material and the filter discharged from the release hole; and
a waste port to guide, from the release hole to the waste container, the solid-phase extraction material and the filter discharged from the release hole.

4. The analyzer according to claim 1, wherein the determining mechanism for filling position comprises:
a rod for moving the filter along the inside of the discharge passage; and
a pressure detection unit for detecting force applied to the rod by the filter as a pressure, when the filter moves forward to the position of the convex or concave portion,
wherein the position of the filter is determined depending on the pressure detected by the pressure detection unit.

5. The analyzer according to claim 4, wherein
an elastic member applies elastic force to the rod in a travelling direction of the rod at a degree not to subject the filter to plastic deformation; and
the rod moves the filter along the inside of the discharge passage by the elastic force.

6. The analyzer according to claim 1, wherein the discharging mechanism is configured to discharge the solid-phase extraction material from a release hole formed at an end of the discharge passage.

7. The analyzer according to claim 6, further comprising:
a waste container to receive the solid-phase extraction material discharged from the release hole; and
a waste port to guide, from the release hole to the waste container, the solid-phase extraction material discharged from the release hole.

8. The analyzer according to claim 6, wherein an inside of the discharge passage has a convex or concave portion; and the solid-phase extraction material in a monolithic structure is locked at the convex or concave portion so as to be packed in the discharge passage.

9. The analyzer according to claim 8, the determining mechanism setting a position of the solid-phase extraction material in the discharge passage at a position of the convex or concave portion.

10. The analyzer according to claim 9, the determining mechanism for filling position comprising:
a rod for moving the solid-phase extraction material along the inside of the discharge passage; and
a pressure detection unit for detecting force applied to the rod by the solid-phase extraction material, as a pressure, when the solid-phase extraction material moves forward to the position of the convex or concave portion,
wherein the position of the solid-phase extraction material is determined depending on the pressure detected by the pressure detection unit.

11. The analyzer according to claim 10, wherein
an elastic member applies elastic force to the rod in a traveling direction of the rod at a degree not to subject the solid-phase extraction material to plastic deformation; and
the rod moves the solid-phase extraction material along the inside of the discharge passage by the elastic force.

12. An analyzer comprising:
a container including:
a body part to receive a sample solution, the sample solution containing a measurement component of analytical target; and
a discharge passage to discharge the sample solution introduced from the body part;
a filling mechanism for a monolithic solid-phase extraction material, the filling mechanism being configured to fill the discharge passage with the monolithic solid-phase extraction material for solid-phase extraction of the measurement component;
a discharging mechanism for discharging the monolithic solid-phase extraction material from the container after the measurement component is subjected to the solid-phase extraction;
a container cleaning mechanism for cleaning the container from which the monolithic solid-phase extraction material is removed, wherein
the discharging mechanism is configured to discharge the monolithic solid-phase extraction material from a release hole formed at an end of the discharge passage;
an inside of the discharge passage has a convex or concave portion; and
the monolithic solid-phase extraction material is locked at the convex or concave portion so as to be packed in the discharge passage; and
the filling mechanism for the monolithic solid-phase extraction material includes a determining mechanism for filling position, the determining mechanism setting a position of the monolithic solid-phase extraction material in the discharge passage at a position of the convex or concave portion.

13. The analyzer according to claim 12, further comprising:
a waste container to receive the monolithic solid-phase extraction material discharged from the release hole; and a waste port to guide, from the release hole to the waste container, the monolithic solid-phase extraction material discharged from the release hole.

14. The analyzer according to claim 12, the determining mechanism for filling position comprising:

a rod for moving the monolithic solid-phase extraction material along the inside of the discharge passage; and a pressure detection unit for detecting force applied to the rod by the monolithic solid-phase extraction material, as a pressure, when the monolithic solid-phase extraction material moves forward to the position of the convex or concave portion, wherein the position of the monolithic solid-phase extraction material is determined depending on the pressure detected by the pressure detection unit.

15. The analyzer according to claim 14, wherein an elastic member applies elastic force to the rod in a traveling direction of the rod at a degree not to subject the monolithic solid-phase extraction material to plastic deformation; and the rod moves the monolithic solid-phase extraction material along the inside of the discharge passage by the elastic force.

* * * * *